United States Patent [19]
Beutler et al.

[11] Patent Number: 5,770,402
[45] Date of Patent: Jun. 23, 1998

[54] DNA ENCODING MACROPHAGE INFLAMMATORY PROTEIN-1γ

[75] Inventors: Bruce A. Beutler; Alexander N. Poltorak, both of Dallas, Tex.

[73] Assignee: Board of Regents, The University of Texas System, Austin, Tex.

[21] Appl. No.: 418,032

[22] Filed: Apr. 5, 1995

[51] Int. Cl.$^6$ ............................ C12N 15/19; C07K 14/52
[52] U.S. Cl. ........................ 435/69.5; 435/71.1; 435/71.2; 435/172.3; 435/325; 435/252.3; 435/252.8; 435/320.1; 536/23.1; 536/23.5; 536/24.31
[58] Field of Search ................................. 435/69.5, 70.1, 435/71.1, 71.2, 172.3, 240.2, 252.3, 252.8, 325, 320.1; 536/23.1, 23.5, 24.31; 935/11, 22, 52, 66, 72, 73

[56] References Cited

FOREIGN PATENT DOCUMENTS 9517092  6/1995  WIPO .

OTHER PUBLICATIONS

Ahuja and Murphy, "Molecular Piracy of Mammalian Interleukin–8 Receptor Type B by Herpesvirus Saimiri," *The Journal of Biological Chemistry*, 268 (28) :20691–20694, 1993.
Ahuja et al., "Chemokine Receptors and Molecular Mimicry," *Immunology Today*, 15(6) :281–287, 1994.
Horuk et al., "The Human Erythrocyte Inflammatory Peptide (Chemokine) Receptor. Biochemical Characterization, Solubilization, and Development of a Binding Assay for the Soluble Receptor," *Biochemistry*, 32:5733–5738, 1993.
Horuk, "The Interleukin–8–Receptor Family: From Chemokines to Malaria," *Immunology Today*, 15 (4):169–174, 1994.
Horuk et al., "A Receptor for the Malarial Parasite *Plasmodium vivax*: The Erythrocyte Chemokine Receptor," *Science*, 261 :1182–1184, Aug. 1993.
Kelvin et al., "Chemokines and Serpentines: The Molecular Biology of Chemokine Receptors," *Journal of Leukocyte Biology*, 54:604–612, Dec. 1993.
Kruys et al., "Translational Control Mediated by UA–Rich Sequences," *Enzyme*, 44:193–202, 1990.
Kuna et al., "Characterization of the Human Basophil Response to Kytokines, Growth Factors, and Histamine Releasing Factors of the INtercrine/Chemokine Family," *The Journal of Immunology*, 150(5) :1932–1943, Mar. 1993.
McColl et al., "Uncoupling of Early Signals Transduction Events from Effector Functin in Human Peripheral Blood Neutrophils in Response to Recombinant Macrophage Inflammatory Proteins–1α and 1β$^1$," *The Journal of Immunology*, 150(10) :4550–4560, May 1993.
Myers et al., "Fever and Feeding: Differential Actions of Macrophage Inflammatory Protein–1 (MIP–1) , MIP–αand MIP–1β on Rat Hypothalamus," *Neurochemical Research*, 18(6) :667–673, 1993.

Neote et al., "Functional and Biochemical Analysis of the Cloned Duffy Antigen: Identity with Red Blood Cell Chemokine Receptor," *Blood*, 84 (1) :44–52, Jul. 1994.
Neote et al., "Molecular Cloning, Functional Expression, and Signaling Characteristics of a C–C Chemokine Receptor," *Cell*, 72:415–525, Feb. 1993.
Neote et al., "Identification of a Promiscuous Inflammatory Peptide Receptor on the Surface of Red Blood Cells," *The Journal of Biological Chemistry*, 268(17) :12247–12249, Jun. 1993.
Oppenheim et al., "Properties of the Novel Proinflammatory Supergene Intercrine Cytokine Family," *Annu. Rev. Immunol.*, 9:617–48, 1991.
Poltorak et al., "Receptor–Mediated Label–Transfer Assay (RELAY) : A Novel Method for the Detection of Plasma Tumor Necrosis Factor at Attomolar Concentrations," *Journal of Immunological Methods*, 169:93–99, 1994.
Ralph, "Some Presentations on TGF–β, MIP–1, and Newly Identified Hematopoietic Inhibitors at the Second International Conference on Negative Regulators of Hematopoiesis," *Lymphokine and Cytokine Research*, 10 (3) :237, 1991.
Schall, et al., "Human Macrophage Inflammatory Protein α (MIP–1α) and MIP–1β Chemokines Attract Distinct Populations of Lymphocytes," *J. Exp. Med.*, 177 :1821–1825, Jun. 1993.
Schall, "Biology of the Rantes/SIS Cytokine Family," *Cytokine*, 3 (3) :165–183, May 1991.
Wang et al., "Identification of RANTES Receptors on Human Monocytic Cells: Competition for Binding and Desensitization by Homologous Chemotactic Cytokines," *The Journal of Experimental Medicine*, 177:699–705, Mar. 1993.
Wang et al., "Human Recombinant Macrophage Inflammatory Protein–1α and –β and Monocyte Chemotactic and Activating Factor Utilize Common an Unique Receptors on Human Monocytes," *The Journal of Immunology*, 150(7):3022–329, Apr. 1993.
Zawada et al., "Fever Evoked bu Macrophage Inflammatory Protein–1 (MIP–1) Injected into Preoptic or Ventral Septal Area of Rats Depends on Intermediary Protein Synthesis," *Brain Research Bulletin*, 3:17–21, 1993.
Orlofsky et al. (1991) Cell. Regulation vol. 2, pp. 403–412.
Berger et al. (1993) DNA & Cell Biology, vol. 12, No. 9, pp. 839–847.
Poltorak et al. (1995) J. of Inflammation, vol. 45 pp. 207–219.

*Primary Examiner*—John Ulm
*Assistant Examiner*—Prema Mertz
*Attorney, Agent, or Firm*—Arnold, White & Durkee

[57] ABSTRACT

Disclosed are novel nucleic acid and peptide compositions comprising a constitutively-expressed CC chemokine. Also disclosed are methods of use for MIP-1γ amino acid sequences and the DNA segments which encode them in the stimulation of an immune response, the production of limited pyrexia, the treatment of proliferative cell disorders and T-cell mediated diseases, and the prophylaxis of bacterial sepsis in an animal.

30 Claims, 13 Drawing Sheets

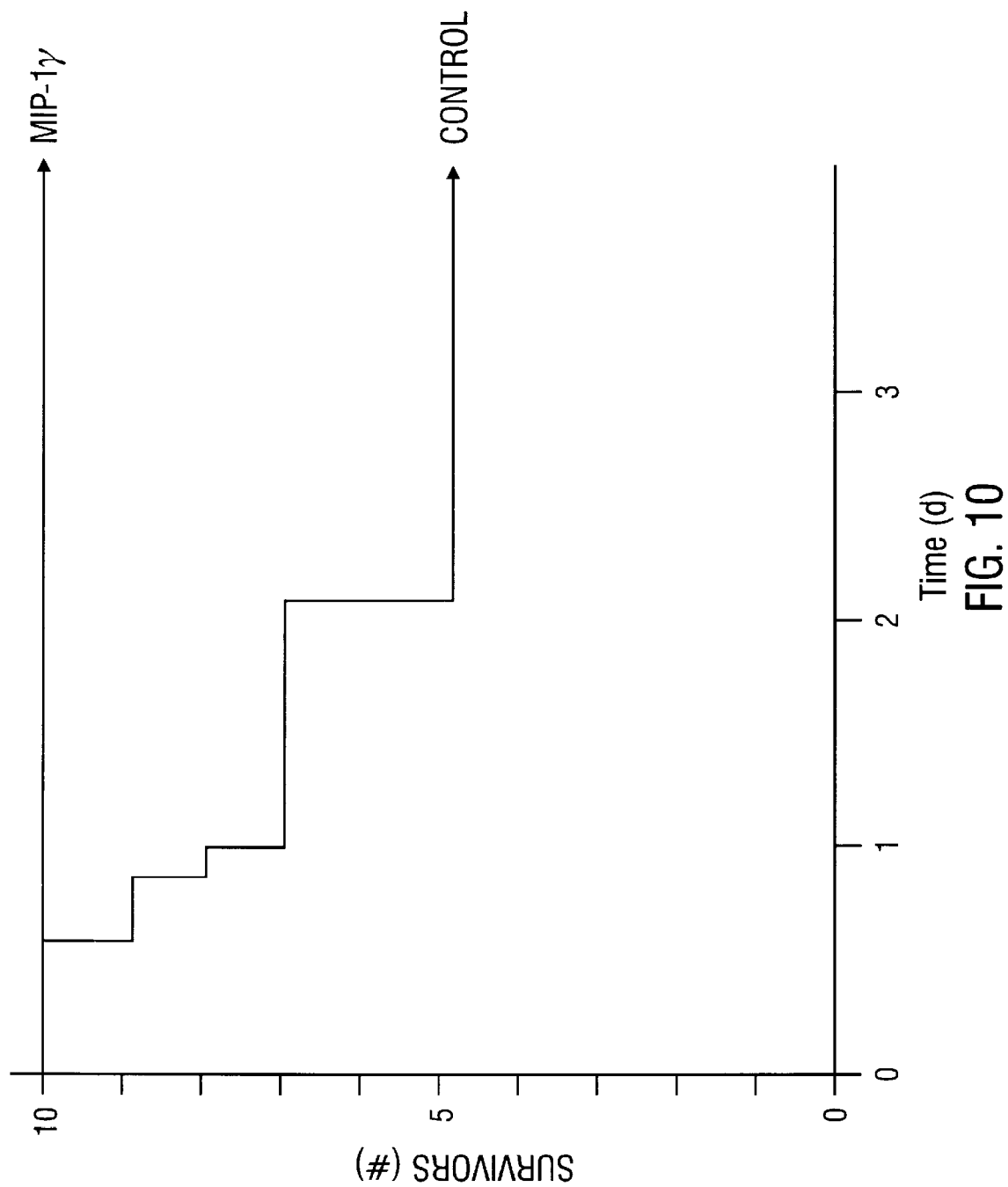

DNA ENCODING MACROPHAGE INFLAMMATORY PROTEIN-1γ

The United States government has certain rights in the present invention pursuant to Grant P01-DK42582 from the National Institutes of Health.

BACKGROUND OF THE INVENTION

A. Field of the Invention

The present invention relates generally to the field of molecular biology. More particularly, certain embodiments concern methods and compositions comprising a novel constitutive cytokine, MIP-1γ. In certain embodiments, the invention concerns the use of MIP-1γ peptides and nucleic acid sequences encoding the MIP-1γ cytokine in the stimulation of an immune response, the prophylaxis of sepsis and the treatment of T-cell mediated diseases including rheumatoid arthritis and multiple sclerosis.

B. Description of the Related Art

1. Inducible Cytokines

The superfamily of small inducible cytokines (chemokines) is divisible into two groups on a phylogenetic basis (Schall, 1991; Ahuja et al., 1994; Oppenheim et al., 1991.). The CXC chemokines (including IL-8, MIP-2, PF-4, and others) each have two cysteines separated by a single amino acid residue, whereas the CC chemokines (including MIP-1α, MIP-1β, C10, RANTES, and others) each have two adjacent cysteines at a similar location. The CC and CXC chemokines bind to a common ("promiscuous") receptor, identified on erythrocytes (Neote et al., 1993; Horuk et al., 1993), and also to group-specific receptors (Horuk, 1994; Neote et al., 1994; Kelvin et al., 1993; Wang et al., 1993; Neote et al., 1993), identified on leukocytes and other cells. Although chemokines of both groups have well-known pro-inflammatory, pyrogenic, chemokinetic, and hematopoietic effects in vitro, the essential functions that chemokines evolved to fulfill in vivo remain unclear.

The chemokine superfamily is structurally redundant, in the sense that more than one ligand may sometimes utilize a single receptor (Schall, 1991; Neote et al., 1993; Horuk et al., 1993; Horuk et al., 1993). Moreover, at least some chemokine receptors have important biological functions beyond their ability to engage chemokines; hence, the Duffy blood group antigen—a promiscuous chemokine receptor— also serves as the *P. vivax* malaria receptor on human erythrocytes (Ahuja et al., 1994; Neote et al., 1993; Neote et al., 1994).

MIP-1α and MIP-1β are perhaps best known as negative modulators of hematopoiesis (Broxmeyer et al., 1993; Broxmeyer, 1990; Ralph, 1991). Both of which are important pyrogens, with the latter being far more potent that the former (Myers et al., 1993; Zawada et al., 1993), as activators and chemoattractants of polymorphonuclear cells (Kuna, 1993; Bischoff et al., 1993; Wolpe et al., 1988; Davatelis et al., 1988; Rot et al., 1992) and lymphocytes (Schall et al., 1993), and as activators of monocyte function (Wang et al., 1993; McColl et al., 1993). Autodesensitization of MIP-1α has been reported previously (McColl et al., 1993), and bespeaks a transient signal induced by receptor binding.

Chemokines of both the CC and CXC families are known to have myelosuppressive activity (Broxmeyer et al., 1990), the most dramatic ramification being the observation of abnormal neutrophilia in mice bearing an IL-8 receptor knockout mutation. Given that chemokines exert a myelosuppressive effect, the identification of a constitutively-expressed high-level cytokine should provide an important opposition to the action of pro-myelopoietic cytokines such as G-CSF and GM-CSF. Such antagonism is common in biological systems (e.g., the insulin vs. glucagon or calcitonin vs. parathyroid hormone interaction).

2. Deficiencies in the Prior Art

In addition to those characteristics described above, all of the chemokines known to date are inducible and are expressed in relatively low concentration. Therefore, what is lacking in the prior art are constitutively expressed, uglycosylated CC-type cytokines, which are tissue specific, expressed in high concentration, and which produce only limited pyrexia.

Methods for the use of such chemokines would facilitate the modulation of calcium flux in certain tissues and the treatment of T-cell mediated diseases such as rheumatoid arthritis, multiple sclerosis, inflammatory bowel disease (e.g., Crohn's disease and ulcerative colitis), allergy, contact hypersensitivity, psoriasis, systemic lupus erythematosus, and diseases mediated by superantigen toxins such as staphylococcal enterotoxin B, toxic shock syndrome toxin 1, and the like.

The development of methods and compositions aimed at prophylactic stimulation of the immune system to treat these disorders, bacterial sepsis, infections, Crohn's disease, and other related disorders, would also represent a major breakthrough in the medical arts. Moreover, such novel chemokines would be useful in the production of limited pyrexia in an animal, and the isolation of CC-type chemokine peptides in large quantity.

Identifying constitutively-expressed tissue-specific cytokines would not only permit an increased understanding of the mechanisms of hematopoiesis regulation, desensitization of the immune response, and neoplasia, but would also open the door to the design of novel therapeutic strategies for cell-specific calcium modulation, regulation of granulopoiesis and hematopoiesis in general, and the treatment of proliferative cell disorders such as human cancer, and particularly leukemias and other sarcomas such as melanoma.

SUMMARY OF THE INVENTION

The present invention overcomes one or more of these and other drawbacks inherent in the prior art by providing novel compositions and methods for their use in prophylaxis of sepsis, production of limited pyrexia, treatment of proliferative disorders and neoplasias, and finally, diagnosis and treatment of T-cell mediated arthritic diseases, including multiple sclerosis.

1. Cytokine and Chemokine Genes

As used herein, the term "cytokine gene" is used to refer to a gene or DNA coding region that encodes a protein, polypeptide or peptide that is capable of promoting, or assisting in the promotion of, cellular activities such as movement, antimicrobial action, adhesion to surfaces, and the induction of other genes (including cytokine genes) that may have many effects, including the induction or release of other cytokines, or alteration of sensitivity to the effects of other cytokines.

A variety of cytokine genes are now known, all of which are suitable for use in connection with the present invention. Cytokine/chemokine-encoding genes and their translation products may include, for example, MIP-1γ, MIP-1β, MIP-1α, C10, gro-α, gro-β, gro-γ, IL-8, MCP, MCAF, and others, and even cytokine receptor genes and the like. Any of the above or other related genes, or DNA segments encoding the active portions of such proteins, may be used in the novel methods of the present invention.

As known to those of skill in the art, the original source of a recombinant gene or DNA segment to be used in a therapeutic regimen need not be of the same species as the animal to be treated. In this regard, it is contemplated that any recombinant cytokine gene may be employed to regulate granulopoiesis or hematopoiesis in general, promote prophylaxis against sepsis and other infections by stimulating an immune response, or by decreasing the severity of such T-cell mediated diseases as rheumatoid arthritis, Crohn's disease, ulcerative colitis, allergy, contact hypersensitivity, psoriasis, systemic lupus erythematosus, multiple sclerosis and the like, promote cell repair or regeneration in a human subject or an animal.

Particularly preferred genes are those isolated from humans. However, since the sequence homology for genes encoding cytokines is conserved across species lines, equine, murine, and bovine species may also be contemplated as sources, in that such genes and DNA segments are readily available, with the human or murine forms of the gene being most preferred for use in human treatment regimens. Recombinant proteins and polypeptides encoded by isolated DNA segments and genes are often referred to with the prefix "r" for recombinant and "rh" for recombinant human. As such, DNA segments encoding rMIP-1γs, or rMIP-1γ-related genes, etc. are contemplated to be particularly useful in connection with this invention. Any recombinant cytokine gene would likewise be very useful with the methods of the invention.

The definition of a "cytokine gene", as used herein, is a gene that hybridizes, under relatively stringent hybridization conditions (see, e.g., Maniatis et al., 1982), to DNA sequences presently known to include cytokine gene sequences. The definition of a "chemokine gene", as used herein, is a gene that hybridizes, under relatively stringent hybridization conditions (see, e.g., Maniatis et al., 1982), to DNA sequences presently known to include chemokine gene sequences.

To prepare a cytokine gene segment or cDNA one may follow the teachings disclosed herein and also the teachings of any of patents or scientific documents specifically referenced herein. One may obtain a rMIP-1γ- or other chemokine/cytokine-encoding DNA segment using molecular biological techniques, such as polymerase chain reaction (PCR™ or screening of a cDNA or genomic library, using primers or probes with sequences based on the above nucleotide sequence. Such fragments may be readily prepared by, for example, directly synthesizing the fragment by chemical means, by application of nucleic acid reproduction technology, such as the PCR™ technology of U.S. Pat. Nos. 4,683,195 and 4,683,202 (herein incorporated by reference). The practice of these techniques is a routine matter for those of skill in the art, as taught in various scientific texts (see e.g., Sambrook et al., 1989), incorporated herein by reference. Certain documents further particularly describe suitable mammalian expression vectors, e.g., U.S. Pat. No. 5,168,050, incorporated herein by reference. The cytokine genes and DNA segments that are particularly preferred for use in certain aspects of the present methods are those encoding MIP-1γ and MIP-1γ-related chemokines.

It is also contemplated that one may clone further genes or cDNAs that encode a cytokine/chemokine peptide, protein or polypeptide. The techniques for cloning DNA molecules, i.e., obtaining a specific coding sequence from a DNA library that is distinct from other portions of DNA, are well known in the art. This can be achieved by, for example, screening an appropriate DNA library which relates to the cloning of a chemokine gene such as MIP-1γ. The screening procedure may be based on the hybridization of oligonucleotide probes, designed from a consideration of portions of the amino acid sequence of known DNA sequences encoding related cytokine proteins. The operation of such screening protocols are well known to those of skill in the art and are described in detail in the scientific literature, for example, see Sambrook et al., 1989, incorporated herein by reference.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the cytokine activity of a protein, to increase its biological stability or half-life, to change its glycosylation pattern, and the like. All such modifications to the nucleotide sequences are encompassed by this invention.

2. MIP-1γ-Encoding DNA Segments

The present invention, in a general and overall sense, concerns the isolation and characterization of a novel gene, mip-1γ which encodes the CC chemokine, MIP-1γ. A preferred embodiment of the present invention is a purified nucleic acid segment that encodes a protein having an amino acid sequence as shown in FIG. 1, and in accordance with SEQ ID NO:2. Another embodiment of the present invention is a purified nucleic acid segment, further defined as including a nucleotide sequence in accordance with SEQ ID NO:1.

In a more preferred embodiment the purified nucleic acid segment consists essentially of the nucleotide sequence of SEQ ID NO:1. As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a mip-1γ coding sequence yet is isolated away from, or purified free from, total genomic DNA, for example, total cDNA or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified mip-1γ gene refers to a DNA segment including mip-1γ coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest, in this case mip-1γ, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a mip-1γ gene, that includes within its amino acid sequence an amino acid sequence in accordance with SEQ ID NO:2. Moreover, in other particular embodiments, the invention concerns isolated DNA segments and recombinant vectors incorporating DNA sequences which encode a gene that includes within its amino acid sequence the amino acid sequence of a mip-1γ gene corresponding to murine mip-1γ.

Another preferred embodiment of the present invention is a purified nucleic acid segment that encodes a protein in accordance with SEQ ID NO:2, further defined as a recombinant vector. As used herein the term, "recombinant vector", refers to a vector that has been modified to contain a nucleic acid segment that encodes a MIP-1γ protein, or a fragment thereof. The recombinant vector may be further defined as an expression vector comprising a promoter operatively linked to said MIP-1γ-encoding nucleic acid segment.

A further preferred embodiment of the present invention is a host cell, made recombinant with a recombinant vector comprising a mip-1γ gene. The recombinant host cell may be a prokaryotic cell. In a more preferred embodiment, the recombinant host cell is a eukaryotic cell. As used herein, the term "engineered" or "recombinant" cell is intended to refer to a cell into which a recombinant gene, such as a gene encoding MIP-1γ, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In certain embodiments, the invention concerns isolated DNA segments and recombinant vectors which encode a protein or peptide that includes within its amino acid sequence an amino acid sequence essentially as set forth in SEQ ID NO:2. Naturally, where the DNA segment or vector encodes a full length MIP-1γ protein, or is intended for use in expressing the MIP-1γ protein, the most preferred sequences are those which are essentially as set forth in SEQ ID NO:2.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene having a sequence essentially as set forth in SEQ ID NO:2, and that is associated with a constitutively-produced chemokine of the CC family. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:2 will be sequences which are "essentially as set forth in SEQ ID NO:2."

In certain other embodiments, the invention concerns isolated DNA segments and recombinant vectors that include within their sequence a nucleic acid sequence essentially as set forth in SEQ ID NO:1. The term "essentially as set forth in SEQ ID NO: 1," is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions will be well known to those of skill in the art and are clearly set forth herein, for example conditions for use with southern and northern blot analysis, and as described in Example 1, and, specifically those, conditions used to generate the data in FIG. 2A and FIG. 2B.

Naturally, the present invention also encompasses DNA segments which are complementary, or essentially complementary, to the sequence set forth in SEQ ID NO:1. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 under relatively stringent conditions such as those described herein in Example 1.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 to 15 or 20, 30, or 40 or so nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

A preferred embodiment of the present invention is a nucleic acid segment which comprises at least a 14-nucleotide long stretch which corresponds to, or is complementary to, the nucleic acid sequence of SEQ ID NO:1. In a more preferred embodiment the nucleic acid is further defined as comprising at least a 20 nucleotide long stretch, a 30 nucleotide long stretch, 50 nucleotide long stretch, 100 nucleotide long stretch, a 200 nucleotide long stretch, a 500 nucleotide long stretch, a 1000 nucleotide long stretch, or at least an 1118 nucleotide long stretch which corresponds to, or is complementary to, the nucleic acid sequence of SEQ ID NO:1. The nucleic acid segment may be further defined as having the nucleic acid sequence of SEQ ID NO:1.

An related embodiment of the present invention is a nucleic acid segment which comprises at least a 14-nucleotide long stretch which corresponds to, or is complementary to, the nucleic acid sequence of SEQ ID NO:1, further defined as comprising a nucleic acid fragment of up to 10,000 basepairs in length. A more preferred embodiment if a nucleic acid fragment comprising from 14 nucleotides of SEQ ID NO:1 up to 5,000 basepairs in length, 3,000 basepairs in length, 1,000 basepairs in length, 500 basepairs in length, or 100 basepairs in length.

Naturally, it will also be understood that this invention is not limited to the particular nucleic acid and amino acid sequences of SEQ ID NOS:1 and 2. Recombinant vectors and isolated DNA segments may therefore variously include the MIP-1γ coding regions themselves, coding regions bearing selected alterations or modifications in the basic coding region, or they may encode larger polypeptides which nevertheless include MIP-1γ-coding regions or may encode biologically functional equivalent proteins or peptides which have variant amino acids sequences.

The DNA segments of the present invention encompass biologically functional equivalent MIP-1γ proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the MIP-1γ protein or to test mip-1γ mutants in order to examine chemokine activity or determine the presence of MIP-1γ of the peptide in various cells and tissues at the molecular level.

A preferred embodiment of the present invention is a purified composition comprising a polypeptide having an amino acid sequence in accordance with SEQ ID NO:2. The term "purified" as used herein, is intended to refer to a MIP-1γ protein composition, wherein the MIP-1γ protein is purified to any degree relative to its naturally-obtainable state, i.e., in this case, relative to its purity within a eukaryotic cell extract. A preferred cell for the isolation of MIP-1γ protein is a macrophage cell, however, MIP-1γ protein may also be isolated from patient specimens, recombinant cells, tissues, isolated subpopulations of tissues, and the like, as will be known to those of skill in the art, in light of the present disclosure. A purified MIP-1γ protein composition therefore also refers to a polypeptide having the amino acid sequence of SEQ ID NO:2, free from the environment in which it may naturally occur.

If desired, one may also prepare fusion proteins and peptides, e.g., where the MIP-1γ coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the mip-1γ gene whether from cDNA based or genomic DNA, one may proceed to prepare an expression system for the recombinant preparation of MIP-1γ protein. The engineering of DNA segment(s) for expression in a prokaryotic or eukaryotic system may be performed by techniques generally known to those of skill in recombinant expression. For example, one may prepare a MIP-1γ-GST (glutathione-S-transferase) fusion protein that is a convenient means of bacterial expression. However, it is believed that virtually any expression system may be employed in the expression of MIP-1γ.

mip-1γ may be successfully expressed in eukaryotic expression systems, however, the inventors aver that bacterial expression systems can be used for the preparation of MIP-1γ for all purposes. The cDNA containing mip-1γ may be separately expressed in bacterial systems, with the encoded proteins being expressed as fusions with β-galactosidase, avidin, ubiquitin, *Schistosoma japonicum* glutathione S-transferase, multiple histidines, epitope-tags and the like. It is believed that bacterial expression will ultimately have advantages over eukaryotic expression in terms of ease of use and quantity of materials obtained thereby.

It is proposed that transformation of host cells with DNA segments encoding MIP-1γ will provide a convenient means for obtaining an MIP-1γ protein. It is also proposed that cDNA, genomic sequences, and combinations thereof, are suitable for eukaryotic expression, as the host cell will, of course, process the genomic transcripts to yield functional MRNA for translation into protein.

Another embodiment is a method of preparing a protein composition comprising growing recombinant host cell comprising a vector that encodes a protein which includes an amino acid sequence in accordance with SEQ ID NO:2, under conditions permitting nucleic acid expression and protein production followed by recovering the protein so produced. The host cell, conditions permitting nucleic acid expression, protein production and recovery, will be known to those of skill in the art, in light of the present disclosure of the mip-1γ gene.

3. Gene Constructs and DNA Segments

As used herein, the terms "gene" and "DNA segment" are both used to refer to a DNA molecule that has been isolated free of total genomic DNA of a particular species. Therefore, a gene or DNA segment encoding a cytokine gene refers to a DNA segment that contains sequences encoding a cytokine protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, a cytokine gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

4. Recombinant Vectors Expressing mip-1γ

A particular aspect of this invention provides novel ways in which to utilize MIP-1γ-encoding DNA segments and recombinant vectors comprising mip-1γ DNA segments. As is well known to those of skill in the art, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a MIP-1γ protein and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate MIP-1γ-encoding gene or DNA molecule, it may be inserted into any one of the many vectors currently known in the art, so that it will direct the expression and production of the MIP-1γ protein when incorporated into a host cell. In a recombinant expression vector, the coding portion of the DNA segment is positioned under the control of a promoter. The promoter may be in the form of the promoter which is naturally associated with a MIP-1γ-encoding gene, as may be obtained by isolating the 5' non-coding sequences located upstream of the coding segment or exon, for example, using recombinant cloning and/or PCR™ technology, in connection with the compositions disclosed herein.

In certain embodiments, it is contemplated that particular advantages will be gained by positioning the MIP-1γ-encoding DNA segment under the control of a recombinant, or heterologous, promoter. As used herein, a recombinant or heterologous promoter is intended to refer to a promoter that is not normally associated with a mip-1γ gene in its natural environment. Such promoters may include those normally associated with other cytokine genes, and/or promoters isolated from any other bacterial, viral, eukaryotic, or mammalian cell. Naturally, it will be important to employ a promoter that effectively directs the expression of the DNA segment in the particular cell containing the vector comprising the MIP-1γ gene.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

5. MIP-1γ Pharmaceutical Compositions

Another aspect of the present invention includes novel compositions comprising isolated and purified MIP-1γ protein or nucleic acids which encode MIP-1γ protein. It will, of course, be understood that one or more than one cytokine gene may be used in the methods and compositions of the invention. The nucleic acid delivery methods may thus entail the administration of one, two, three, or more, cytokine genes. The maximum number of genes that may be applied is limited only by practical considerations, such as the effort involved in simultaneously preparing a large number of gene constructs or even the possibility of eliciting an adverse cytotoxic effect.

The particular combination of genes may be two or more distinct cytokine genes; or it may be such that a cytokine gene is combined with another gene and/or another protein such as a cytoskeletal protein, cofactor or other biomolecule; a hormone or growth factor gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same or different types. Thus, an almost endless combination of different genes and genetic constructs may be employed. Certain gene combinations may be designed to, or their use may otherwise result in, achieving synergistic effects on cell growth and/or stimulation of an immune response. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic acid segment or gene encoding a cytokine could be administered in combination with further agents, such as, e.g., proteins or polypeptides or various pharmaceutically active agents. So long as the composition comprises a cytokine gene, there is virtually no limit to other components which may also be included, given that the additional agents do not cause a significant adverse effect upon contact with the target cells or host tissues. The nucleic acids may thus be delivered along with various other agents as required in the particular instance.

Pharmaceutical compositions prepared in accordance with the present invention find use in preventing or ameliorating sepsis in an animal exposed to bacterial lipopolysaccharide. Such methods generally involve administering to an animal a pharmaceutical composition comprising an immunologically effective amount of a MIP-1γ composition. This composition may include an immunologically-effective amount of either a MIP-1γ peptide or a MIP-1γ-encoding nucleic acid composition. Such compositions may also be used to generate an immune response in an animal.

Therapeutic kits comprising MIP-1γ peptides or MIP-1γ-encoding nucleic acid segments comprise another aspect of the present invention. Such kits will generally contain, in suitable container means, a pharmaceutically acceptable formulation of MIP-1γ peptide or a MIP-1γ-encoding nucleic acid composition. The kit may have a single container means that contains the MIP-1γ composition or it may have distinct container means for the MIP-1γ composition and other reagents which may be included within such kits.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

In related embodiments, the present invention contemplates the preparation of diagnostic kits that may be employed to detect the presence of MIP-1γ proteins or peptides and/or antibodies in a sample. Generally speaking, kits in accordance with the present invention will include a suitable MIP-1γ protein or peptide or antibody directed against such a protein or peptide, together with an immunodetection reagent and a means for containing the antibody or antigen and reagent. The components of the diagnostic kits may be packaged either in aqueous media or in lyophilized form.

The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably aliquoted. Where a second binding ligand is provided, the kit will also generally contain a second vial or other container into which this ligand or antibody may be placed. The kits of the present invention will also typically include a means for containing the antibody, antigen, and reagent containers in close confinement for commercial sale. Such containers may include injection or blow-molded plastic containers into which the desired vials are retained.

6. Methods of DNA Transfection

Technology for introduction of DNA into cells is well-known to those of skill in the art. Four general methods for delivering a gene into cells have been described: (1) chemical methods (Graham and VanDerEb, 1973); (2) physical methods such as microinjection (Capecchi, 1980), electroporation (Wong and Neumann, 1982; Fromm et al., 1985) and the gene gun (Yang et al., 1990); (3) viral vectors (Clapp, 1993; Danos and Heard, 1992; Eglitis and Anderson, 1988); and (4) receptor-mediated mechanisms (Wu et al., 1991; Curiel et al., 1991; Wagner et al., 1992).

7. Liposomes and Nanocapsules

The formation and use of liposomes is generally known to those of skill in the art (see for example, Couvreur et al., 1991 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Chonn, 1987).

Nanocapsules can generally entrap compounds in a stable and reproducible way (Henry-Michelland et al., 1987). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1984; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

In addition to the teachings of Couvreur et al. (1991), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

8. MIP-1γ Compositions and Proliferative Cell Disorders

Another aspect of the present invention is the use of MIP-1γ as an antagonist of proliferative cell disorders. The identification and characterization of a novel cytokine which is constitutively expressed in high level in vivo indicates the importance of MIP-1γ's utility as an antagonist of myelopoiesis, and hence proliferative cell disorders including such malignantly transformed cells of myelopoietic origin as acute granulocytic leukemia, chronic granulocytic leukemia, myelocytic leukemia, and other related disorders.

In related aspects, it is expected that MIP-1γ, by interacting with the receptor for some other chemokines, and blocking or desensitizing signal transduction through that receptor, may exert an antagonistic effect on tumor growth. That the gro chemokine (a member of the CXC family) has been identified as an autocrine growth factor for melanoma cells indicates a distinct importance of MIP-1γ and its interaction with chemokine receptors.

Alternatively, blockade of MIP-1γ, inactivation of the mip-1γ gene, or modification of the MIP-1γ cytokine itself may also affect the growth of tumors and be important for anti-cancer therapeutics directed against tumorigenesis.

Further aspects of the present invention include the importance of MIP-1γ as and agonist or antagonist of a variety of inflammatory diseases such as those observed in rheumatoid arthritis, inflammatory bowel disease, psoriasis, systemic lupus erythematosus, multiple sclerosis, and any of a host of other diseases. Of particular importance are the novel methods and diagnostic kits disclosed herein which comprise MIP-1γ as a marker for the diagnosis and monitoring of such inflammatory diseases. The inventors contemplate the use of MIP-1γ assays in determining the over- or under-production of this cytokine and its involvement in such disorders.

9. MIP-1γ Compositions and Production of Limited Pyrexia

Another aspect of the present invention relates to the administration of MIP-1γ to an animal for the production of limited pyrexia. Such a method generally involves administering to the animal a pharmaceutical composition comprising an amount of a MIP-1γ composition (either a nucleic acid composition encoding a MIP-1γ peptide or a MIP-1γ peptide composition itself) necessary to produce a pyrogenic response in such an animal. The administration of MIP-1γ compositions for achieving such a low-grade pyrogenic response is far superior to the administration of compositions comprising other chemokines such as MIP-1α or MIP-1β both of which are potent pyrogenic chemokines capable of inducing extensive pyrexia in an animal in vivo. The limited availability of MIP-1γ to cross the blood-brain barrier enhances the capacity of MIP-1γ to produce a substantially less-threatening and more limited fever or pyrexia in an animal. The term "limited pyrexia" is defined as an elevation of body temperature, or fever, in an animal to a level that is from about 0.5° C. to about 1.5° C. above normal body temperature for such an animal.

10. MIP-1γ Compositions and the Release of Intracellular Calcium

The compositions of the present invention are also contemplated to be useful in the in vitro and in vivo release of intracellular calcium stores from cells such as neutrophils. As illustrated in FIG. 7, MIP-1γ compositions are able to alter or modulate the normal calcium release (or calcium flux) from such cells when an effective amount of MIP-1γ is provided to such cells. For a variety of therapeutic and diagnostic reasons, such a modulation in intracellular $Ca^{++}$ levels may be achieved as a result of primary chemokine stimulation with MIP-1γ peptide or MIP-1γ-encoding DNA compositions.

11. Expression of MIP-1γ

For the expression of MIP-1γ, once a suitable (full-length if desired) clone or clones have been obtained, whether they be cDNA based or genomic, one may proceed to prepare an expression system for the recombinant preparation of MIP-1γ. The engineering of DNA segment(s) for expression in a prokaryotic or eukaryotic system may be performed by techniques generally known to those of skill in recombinant expression. It is believed that virtually any expression system may be employed in the expression of MIP-1γ.

MIP-1γ may be successfully expressed in eukaryotic expression systems, however, it is also envisioned that bacterial expression systems may be preferred for the preparation of MIP-1γ for all purposes. The cDNA for MIP-1γ may be separately expressed in bacterial systems, with the encoded proteins being expressed as fusions with β-galactosidase, ubiquitin, Schistosoma japonicum glutathione S-transferase, and the like. It is believed that bacterial expression will ultimately have advantages over eukaryotic expression in terms of ease of use and quantity of materials obtained thereby.

It is proposed that transformation of host cells with DNA segments encoding MIP-1γ will provide a convenient means for obtaining MIP-1γ peptide. Both cDNA and genomic sequences are suitable for eukaryotic expression, as the host cell will, of course, process the genomic transcripts to yield functional MRNA for translation into protein.

It is similarly believed that almost any eukaryotic expression system may be utilized for the expression of MIP-1γ, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes MIP-1γ, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of MIP-1γ in accordance herewith. Examples include cell lines typically employed for eukaryotic expression such as 239, AtT-20, HepG2, VERO, HeLa, CHO, WI 38, BHK, COS-7, RIN and MDCK cell lines.

It is contemplated that MIP-1γ may be "overexpressed", i.e., expressed in increased levels relative to its natural expression in human cells, or even relative to the expression of other proteins in a recombinant host cell containing MIP-1γ-encoding DNA segments. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural MIP-1γ-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a MIP-1γ peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventors have noticed that the level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

12. Enhanced Production of MIP-1γ

One of the problems with MIP-1γ isolated from natural sources is low yields and extensive purification processes. An aspect of the present invention is the enhanced production of MIP-1γ by recombinant methodologies in a bacterial host, employing DNA constructs to transform Gram-positive or Gram-negative bacterial cells. For example, the use of *Escherichia coli* expression systems are well known to those of skill in the art, as is the use of other bacterial species such as *Bacillus subtilis* or *Streptococcus sanguis*.

Further aspects of the invention include high expression vectors incorporating DNA encoding the novel MIP-1γ and its variants. It is contemplated that vectors providing enhanced expression of MIP-1γ in other systems such as *S. mutans* will also be obtainable. Where it is desirable, modifications of the physical properties of MIP-1γ may be sought to increase its solubility or expression in liquid culture. The mip-1γ locus may be placed under control of a high expression promoter or the components of the expression system altered to enhance expression.

13. MIP-1γ Antibodies

In another aspect, the present invention contemplates an antibody that is immunoreactive with a polypeptide of the invention. An antibody can be a polyclonal or a monoclonal antibody. In a preferred embodiment, an antibody is a monoclonal antibody. Means for preparing and characterizing antibodies are well known in the art (See, e.g., Howell and Lane, 1988).

Briefly, a polyclonal antibody is prepared by immunizing an animal with an immunogen comprising a polypeptide of comprising a polypeptide of the present invention and animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for MIP-1γ may be prepared using conventional immunization techniques, as will be generally known to those of skill in the art. A composition containing antigenic epitopes of MIP-1γ can be used to immunize one or more experimental animals, such as a rabbit or mouse, which will then proceed to produce specific antibodies against MIP-1γ. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a MIP-1γ composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired MIP-1γ peptide.

Following immunization, spleen cells are removed and fused, using a standard fusion protocol with plasmacytoma cells to produce hybridomas secreting monoclonal antibodies against MIP-1γ. Hybridomas which produce monoclonal antibodies to the selected antigens are identified using standard techniques, such as ELISA and Western blot methods. Hybridoma clones can then be cultured in liquid media and the culture supernatants purified to provide the MIP-1γ-specific monoclonal antibodies.

It is proposed that the monoclonal antibodies of the present invention will find useful application in standard immunochemical procedures, such as ELISA and Western blot methods, as well as other procedures which may utilize antibody specific to MIP-1γ epitopes.

Additionally, it is proposed that monoclonal antibodies specific to the particular chemokine may be utilized in other useful applications. For example, their use in immunoabsorbent protocols may be useful in purifying native or recombinant MIP-1γ species or variants thereof.

In general, both poly- and monoclonal antibodies against MIP-1γ may be used in a variety of embodiments. For example, they may be employed in antibody cloning protocols to obtain cDNAs or genes encoding MIP-1γ or related proteins. They may also be used in inhibition studies to analyze the effects of MIP-1γ in cells or animals. Anti-MIP-1γ antibodies will also be useful in immunolocalization studies to analyze the distribution of MIP-1γ during various cellular events, for example, to determine the cellular or tissue-specific distribution of the MIP-1γ peptide under different physiological conditions. A particularly useful application of such antibodies is in purifying native or recombinant MIP-1γ, for example, using an antibody affinity column. The operation of all such immunological techniques will be known to those of skill in the art in light of the present disclosure.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 10. Kaplan-Meier plot of mouse survival following LPS injection. Ten mice in each group received LPS injection. The test group also received injections of MIP-1γ.

DETAILED DESCRIPTION OF THE PREFERRED EMBODIMENTS

Figure 1:
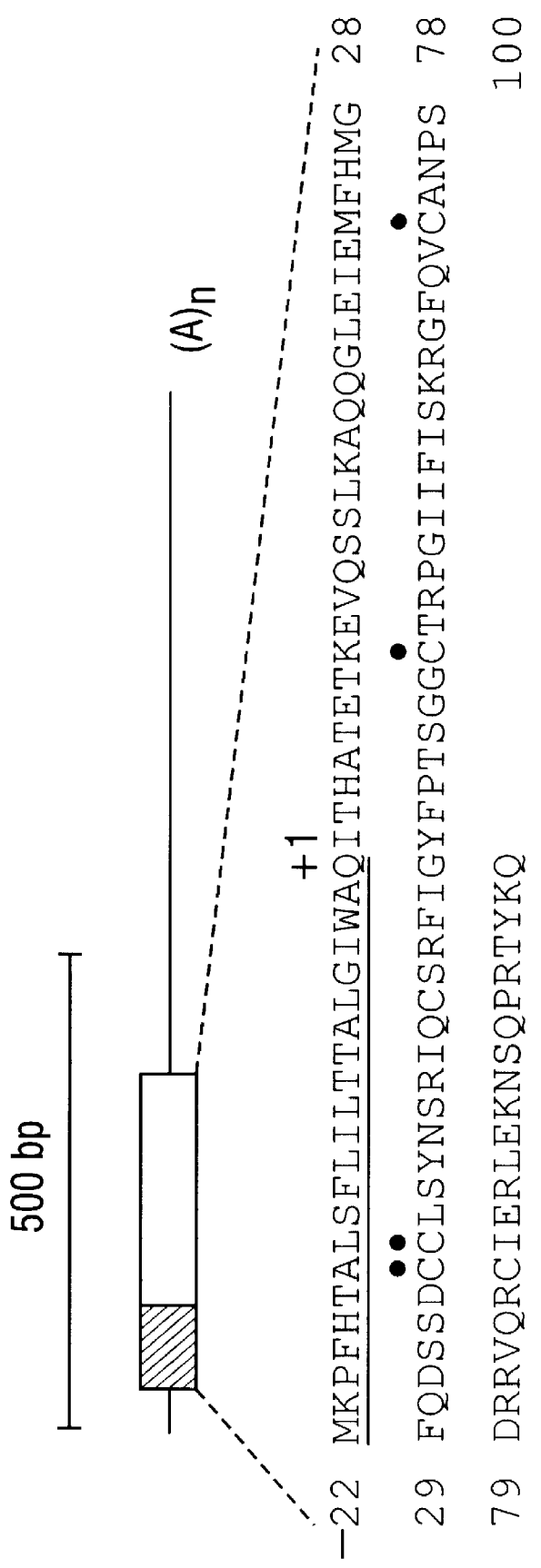
FIG. 1. Predicted amino acid sequences of MIP-1γ. The cDNA sequence is shown in SEQ ID NO:1; none of the repetitive octameric elements TTATTTAT (SEQ ID NO:3) (Caput et al., 1986) typically observed in cytokine cDNA 3'-UTR sequences was present. Two potential polyadenylation signal sequences were seen in the distal 3'-UTR). The putative propeptide, bearing a hydrophobic element that could serve as a signal peptide, is shown as a solid bar, and the mature protein sequence is shown as an open bar in the illustration. Residues comprising the supposed propeptide sequence are underlined, and the cysteines within the mature protein are overscored with dots.

Using a method of differential screening directed toward the isolation of cDNAs encoded by extinguishable genes, the present invention concerns the isolation, cloning, expression, and characterization of a novel CC chemokine family member, designated MIP-1γ.

A. CHEMOKINES

The chemokine superfamily encompasses a subset of cytolines with a point of common origin in evolution, indicated by persistent sequence homology. It has been noted that two general divisions of chemokines exist: those with two adjacent cysteine residues in the polypeptide chain (the CC chemokines), and those which, at the corresponding position in the chain, have an interposed amino acid (the CXC chemokines).

So far as is known, chemokines exert all of their biological effects by binding to specific plasma membrane receptors, and these receptors are all eight-spanning plasma membrane proteins. At least one CC-chemokine specific receptor, two CXC-specific receptors, and one common or "promiscuous" chemokine receptor (capable of binding both CC and CXC chemokines) have been identified.

Chemokines are produced by cells of diverse ontogenic derivation, but in particular, are known to be produced by cells of the immune system (especially macrophages and lymphocytes). With the exception of MIP-1γ, the chemokines are not produced by quiescent cells, but are produced by cells that have been activated using a particular stimulus (e.g., a mitogen or specific antigen applied to lymphocytes, or bacterial lipopolysaccharide applied to macrophages). Once produced, and once bound to their cognate receptors on neutrophils, basophils, eosinophils, lymphocytes, or unspecified cells in the brain, chemokines elicit a number of biological effects, including the stimulation of cell migration, the release of intracellular calcium stores, supression of myelopoiesis, augmentation of tumor cell growth, and the promotion of a pyrexic response in an animal.

B. DIFFERENCES BETWEEN MIP-1γ AND OTHER CYTOKINES

1. MIP-1γ is Expressed Constitutively

Although cloned from a macrophage cDNA library, MIP-1γ is widely expressed in a constitutive fashion, and circulates at high concentrations in the blood of healthy animals. It shares the MIP-1γ receptor on neutrophils, behaves as an agonist in assays of pyrogenicity and neutrophil calcium release, and presumably occupies most of the available chemokine binding sites in the intravascular compartment of normal animals. This is the only chemokine discovered to date which is produced constitutively by quiescent cells.

2. MIP-1γ is Minimally Induced in Response to LPS

MIP-1γ is related to the MIP-1 and C10 proteins, and distantly related to RANTES. While MIP-1γ is encoded by a major MRNA species in unstimulated RAW 264.7 macrophages, as well as primary macrophages, it is minimally induced in response to LPS, both in culture and in vivo. Surprisingly therefore, the MIP-1γ MRNA differs substantially from the MIP-1α and MIP-1β mRNAs, which are of very low abundance in resting cells, but strongly induced by LPS.

To date, only a single leukocyte receptor specific for CC chemokines has been cloned (Neote et al., 1993), but the identity of this receptor relative to that of the present invention remains unknown. Furthermore, it is not known whether other receptors may be utilized by MIP-1γ, although receptor competition studies suggest that some binding sites may be shared.

The fact that both MIP-1α and MIP-1γ activate neutrophil calcium flux, and the fact that each desensitizes cells to the effects of the other, indicates that the two proteins may, however, be somewhat similar in their mode of action.

3. MIP-1γ Lacks Canonical Translation Suppression Sequence

In addition to the unusual regulation of MIP-1γ, which is expressed constitutively by a number tissues in vivo, the mip-1γ gene encoding it lacks the canonical sequence for translation suppression, providing further evidence that this new cytokine is very different from that of its homologs. (For reviews of translation suppression and identification of the canonical sequence responsible, see, e.g., Caput et al., 1986; Kruys et al., 1993; Kruys et al., 1989; Kruys et al., 1988; and Kruys et al., 1987).

4. High Plasma Concentration of MIP-1γ

Unlike any other cytokine reported to date, MIP-1γ is constitutively expressed, circulating in plasma at a concentration that far exceeds the $K_d$ for receptor binding. As such, it is reasonable to conclude that MIP-1γ actually engages the majority of neutrophil CC chemokine receptors. It may be calculated that approximately 70% of the total receptor population is occupied at equilibrium in the presence of a 90 nM steady-state free MIP-1γ concentration (corresponding to 1 μg/ml in plasma). Therefore, a smaller population of receptors is available for engagement by other chemokines. More importantly, continuous down-regulation of response will be observed given constant engagement of the receptor population by MIP-1γ.

5. MIP-1γ Target Cell Desensitization is Unique

It is known that another cytokine, IL-1 is blocked in its action by the presence of the homologous cytokine known as the IL-1 receptor antagonist (IL-1ra). IL-1ra acts by binding to the IL-1 receptors on cells, exerting no agonist effect of its own, but blocking the subsequent binding of IL-1. MIP-1γ blocks the action of other chemokines by an entirely distinct, post-receptor mechanism. Unlike IL-1ra, MIP-1γ is a potent agonist, which, however, elicits rapid desensitization of target cells, leaving them unable to respond to further chemokine stimulation.

6. MIP-1γ MRNA is Absent in Brain Tissue

Although MIP-1γ MRNA accumulates to high levels in the heart and lungs in response to LPS, (and as such, may mediate some of the well-known effects of LPS in these tissues), MIP-1γ MRNA is notably absent in brain tissue, whether or not LPS has been administered peripherally. MIP-1γ protein is also undetectable in the cerebrospinal fluid of normal rats and mice, though it is readily detectable in plasma. This observation would suggest that, under normal circumstances, MIP-1γ does not cross the blood-brain barrier. Consistent with this fact, the peripheral injection of MIP-1γ, unlike peripheral injection of other chemokines, fails to elicit fever. The absence of MIP-1γ MRNA and protein in the central nervous system suggests that tissues in this compartment have not been desensitized to MIP-1γ, or to other chemokines that share its receptors. Therefore, tissues of the central nervous system ought to be able to respond to the introduction or local production of MIP-1γ, should it ever occur. Correspondingly, CNS production or administration of MIP-1γ, while initially provoking a febrile response, may thereafter prevent the initiation of fever by other chemokines of peripheral origin.

C. ELISAs

ELISAs may be used in conjunction with the invention. In an ELISA assay, proteins or peptides incorporating MIP-1γ antigenic sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

D. EPITOPIC CORE SEQUENCES

The present invention is also directed to protein or peptide compositions, free from total cells and other peptides, which comprise a purified protein or peptide which incorporates an epitope that is immunologically cross-reactive with one or more anti-MIP-1γ antibodies.

As used herein, the term "incorporating an epitope(s) that is immunologically cross-reactive with one or more anti-MIP-1γ antibodies" is intended to refer to a peptide or protein antigen which includes a primary, secondary or tertiary structure similar to an epitope located within a MIP-1γ polypeptide. The level of similarity will generally be to such a degree that monoclonal or polyclonal antibodies directed against the MIP-1γ polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of MIP-1γ epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic MIP-1γ-derived peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to MIP-1γ and MIP-1γ-related sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on transferrin-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic MIP-1γ peptides and peptide analogs in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

E. IMMUNOPRECIPITATION

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

F. WESTERN BLOTS

The compositions of the present invention will find great use in immunoblot or western blot analysis. The anti-MIP-1γ antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

G. VACCINES

The present invention contemplates vaccines for use in both active and passive immunization embodiments. Immunogenic compositions, proposed to be suitable for use as a vaccine, may be prepared most readily directly from immunogenic MIP-1γ peptides prepared in a manner disclosed herein. Preferably the antigenic material is extensively dialyzed to remove undesired small molecular weight molecules and/or lyophilized for more ready formulation into a desired vehicle.

The preparation of vaccines which contain MIP-1γ peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The MIP-1γ MIP-1γ-derived peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

H. DNA SEGMENTS

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a MIP-1γ peptide in its natural environment. Such promoters may include promoters normally associated with other genes, and/or promoters isolated from any viral, prokaryotic (e.g., bacterial), eukaryotic (e.g., fungal, yeast, plant, or animal) cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the Pichia expression vector system (Pharmacia LKB Biotechnology), a baculovirus system for expression in insect cells, or any suitable yeast or bacterial expression system.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of MIP-1γ peptides or epitopic core regions, such as may be used to generate anti-MIP-1γ antibodies, also falls within the scope of the invention. DNA segments that encode MIP-1γ peptide antigens from about 10 to about 100 amino acids in length, or more preferably, from about 20 to about 80 amino acids in length, or even more preferably, from about 30 to about 70 amino acids in length are contemplated to be particularly useful.

In addition to their use in directing the expression of MIP-1γ peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least an about 14-nucleotide long contiguous sequence that has the same sequence as, or is complementary to, an about 14-nucleotide long contiguous DNA segment of SEQ ID NO:1 will find particular utility. Longer contiguous identical or complementary sequences, e.g., those of about 20, 30, 40, 50, 100, 200, 300, 500, 1000, (including all intermediate lengths) and even those up to and including about 1118-bp (full-length) sequences will also be of use in certain embodiments.

The ability of such nucleic acid probes to specifically hybridize to MIP-1γ-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15–20, 30, 40, 50, or even of about 100 to about 200 nucleotides or so, identical or complementary to the DNA sequence of SEQ ID NO:1, are particularly contemplated as hybridization probes for use in, e.g., Southern and Northern blotting. Smaller fragments will generally find use in hybridization embodiments, wherein the length of the contiguous complementary region may be varied, such as between about 10–14 and up to about 100 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR™, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02M to about 0.15M NaCl at temperatures of about 50° C. to about 70° C. Such selective conditions tolerate little, if any, mismatch between the probe and the template or target strand, and would be particularly suitable for isolating MIP-1γ-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal, 1976; Prokop, 1991; and Kuby, 1994, are particularly relevant.

Of course, for some applications, for example, where one desires to prepare mutants employing a mutant primer strand hybridized to an underlying template or where one seeks to isolate MIP-1γ-encoding sequences from related species, functional equivalents, or the like, less stringent hybridization conditions will typically be needed in order to allow formation of the heteroduplex. In these circumstances, one may desire to employ conditions such as about 0.15M to about 0.9M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

I. BIOLOGICAL FUNCTIONAL EQUIVALENTS

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glyaine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

J. SITE-SPECIFIC MUTAGENESIS

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

K. MONOCLONAL ANTIBODIES

Means for preparing and characterizing antibodies are well known in the art (See, e.g., Harlow and Lane, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bisbiazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MIP-1γ protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986;

Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

M. PHARMACEUTICAL COMPOSITIONS

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

MOLECULAR CLONING OF A NOVEL CC CHEMOKINE cDNA BY DIFFERENTIAL SCREENING BASED ON EXTINCTION

A. MATERIALS AND METHODS

1. Materials

Recombinant MIP-1α, used for studies of calcium flux in neutrophils, was obtained from R&D Systems (Minneapolis, Minn.). Purified macrophage-derived MIP-1α, used in binding studies, was the kind gift of Dr. Barbara Sherry (Picower Institute, Manhasset, N.Y.). Concanavalin-A was obtained from Sigma (St. Louis, Mo.).

2. Cell lines

NIH 3T3 cells and RAW 264.7 cells, originally obtained from the American Type Culture Collection (Rockville, Md.), were maintained and passaged Dulbecco's modified Eagle's medium (DMEM) supplemented with 5% (RAW 264.7 cells) or 10% (NIH 3T3 cells) fetal bovine serum (FBS). Fusion hybrid cells, produced by fusing G418-resistant RAW 264.7 cells to methotrexate-resistant NIH 3T3 cells, were prepared and characterized as previously described (Kruys et al., 1993).

3. MRNA preparation mRNA for use in cDNA library construction or blot hybridization analysis was isolated from cultured cells using an NP40 lysis method as detailed elsewhere (Sambrook et al., 1989). RNA was harvested from tissues using a guanidinium isothiocyanate homogenization procedure (Sambrook et al., 1989).

4. Blot Hybridization Analysis

20-$\mu$g MRNA samples were denatured using glyoxal and subjected to electrophoresis in agarose. Transfer to nylon was accomplished by electroblotting, and followed by ultraviolet crosslinking (Church and Gilbert, 1984). An antisense riboprobe, produced by transcribing MIP-1$\gamma$, MIP-1$\alpha$, or GAPDH inserts using SP6 or T7 polymerase, was used to detect the respective mRNA species (Maniatis et al., 1982). Hybridization was carried out in the presence of 50% formamide in 5×SSPE, 0.5% SDS, at 65° C. for 12 hr. The blots were subjected to two cycles of washing at 72° C. in 2×SSPE+0.1% SDS, and in 0.1×SSPE+0.1% SDS for 20 min each prior to autoradiography.

5. cDNA library

A cDNA library was constructed from RAW 264.7 cell MRNA using pSPORT-1™ (Life Technologies, Gaithersburg, Md.) as a cloning vector. pSPORT-1™ was designed for bidirectional sequencing from T7 and M13 primer sites, and could also be used for direct production of oligonucleotide probes. Cytoplasmic poly-(A)+ mRNA was isolated from RAW 264.7 cells by NP40 lysis and chromatography using oligo-dT cellulose (Cell Products, Inc. Bedford, Mass.) (Sambrook et al., 1989). The first strand cDNA was synthesized by reverse transcription of poly-(A)+ RNA using an oligo-dT/NotI primer/adapter. The second strand cDNA was synthesized from the DNA-RNA hybrids using RNase H, DNA polymerase, and DNA ligase (Life Technologies, Inc.). The cDNA was then ligated with SalI adapters, fractionated on Sephacryl®-200, and ligated into SalI/NotI digested pSPORT. The complexity of the library prior to amplification was estimated at $1.0 \times 10^6$ independent clones, and the mean insert size, determined by isolation of several dozen cloned fragments of DNA, was estimated at 1.4 kb.

The library was plated at a density of $1 \times 10^3$ colonies per 16 cm plate, and screened using a probe made by random-priming cDNA made from RAW 264.7×NIH 3T3 hybrid cells. Total cDNA probe was prepared using poly A+ RNA isolated from these cells with NP-40™ (Sambrook et al., 1989), random primers, and Klenow polymerase. Briefly, 1 $\mu$g of poly A+ RNA was incubated at 65° C. for 5 min then 1 $\mu$l of a random primer mixture was added and the sample was placed on ice. The reaction was incubated for 1 hr, after which 3 $\mu$l of 3M NaOH was added and the mixture was incubated for 30 min at 65° C. cDNA probe was extracted with phenol/chloroform and purified by spin-dialysis through P-10 beads (Bio-Rad). Probe was added to 50 ml of 6×SSC, 5×Denhardt's, 0.1% SDS, which was used for hybridization.

Colonies that did not hybridize with the probe were selected for further analysis, and clones that were strongly extinguished by cell fusion were identified by Northern blot hybridization, in which the intensity of signal in a lane of RAW 264.7 cell RNA was compared with the intensity of signal in a parallel lane of hybrid cell RNA.

6. Polymerase Chain Reaction

A full-length copy of the MIP-1$\gamma$ cDNA was obtained by PCR™ (42° C., 1 min; 72° C., 1.5 min; 96° C., 0.5 min×30 cycles), applied to the library, and primed using an upstream vector sequence (5'-ATAAGAATGCGGCCGCTGTTGA-CAAAGCCAGATATG-3') (SEQ ID NO:4) and an internal sequence within the initial cDNA clone (5'-AACAGCTATGACCATG-3') (SEQ ID NO:5). A longer representative of the MIP-1$\gamma$ cDNA was thus amplified, subcloned, and sequenced.

7. DNA Sequencing

The MIP-1$\gamma$ cDNA clone was partially sequenced from each end using the Sequenase™ 1.0 kit (Amersham, Arlington Heights, Ill.) and M13 and T7 primers. The complete sequence was obtained using a succession of synthetic oligonucleotides as internal primers. First strand primers were: 5'-ACAGCTATGACCATG-3' (SEQ ID NO:6); 5'-GGCCGGGCATCATCTTTA-3' (SEQ ID NO:7); and 5'-ATGGCTTGGTGGTTAAGA-3' (SEQ ID NO:8). Second strand primers used included: 5'-GTAAAACGACGGCCAGT-3' (SEQ ID NO:9); 5'-TTGAACTCACTAAGACTCC-3' (SEQ ID NO:10); and 5'-GTTTCGGTCTATCAG-3' (SEQ ID NO:11). Both strands were fully covered, and comparisons to existing sequences were made using the FASTA and BLAST search algorithms (Pearson and Lipman, 1988) in the EMBL and GenBank databases.

8. Expression in *E. coli*

Recombinant murine MIP-1$\gamma$ was produced in *E. coli* by linking a PCR™-amplified cDNA fragment encoding the mature form of the molecule to a T7 promoter in the pET-15b expression plasmid (Novagen, Madison, Wis.). This vector incorporates a T7 promoter and a poly-histidine tract and a thrombin-sensitive cleavage site, both in frame and upstream from the cloning site. Primers (5'→3') for PCR™ were:

(a) Upstream: (NdeI site indicated in bold)

5'-GGGAATTCCATATGATCACACATGCAACAGAG-ACA-3' (SEQ ID NO:12); and (b) Downstream: (BamHI site indicated in bold)

5'-CGCGGATCCTATCACACCCTTCTCTAAAGCAA-ATG-3' (SEQ ID NO:13)

Transfected BL21(DE3)pLysS cells (Novagen) were grown to a density of 0.5 ($OD_{600}$). The synthesis of recombinant MIP-1$\gamma$ was induced by addition of isopropylthiogalactoside (IPTG) to a final concentration of 1.0 mM. The cells were allowed to grow for four hr, and then harvested. Cells were lysed by freezing, thawing, and sonication in 1/20 initial culture volume of a solution containing 20 mM Tris, pH 7.9, 0.5M NaCl, and 1 mM PMSF (Buffer A).

The lysate was centrifuged for 10 min at 10,000×g for 10 min at 0° C. The precipitate was washed twice in Buffer A, with repeated centrifugation as above. The pellet was then dissolved in Buffer A, supplemented with 8M urea. It was dialyzed overnight against Buffer A supplemented with 2M urea. 50 bed-volumes of solution were then passed over one bed-volume of a Ni-agarose column (Novagen). The column was washed with 10 bed-volumes of Buffer A containing 2M urea. The bound protein was eluted using a continuous gradient of imidazole, from 0 to 200 mM concentration in Buffer A containing 2M urea. Fractions were assayed for protein and assayed by SDS-polyacrylamide gel electrophoresis (Laemmli, 1970).

Pooled fractions containing purified MIP-1$\gamma$ were dialyzed against a series of declining urea concentrations (1M, 0.5M, 0.25M, 0.125M, and 0M) in 0.1M Na-phosphate buffer, pH 7.8. The purified protein was cleaved with thrombin (Sigma) dissolved at a weight ratio of 1 part thrombin to 2,000 parts MIP-1$\gamma$ for one hr (hr) at room temperature.

The purified protein was frozen at −70° C. in small aliquots. From one liter of culture, 5 mg of purified MIP-1$\gamma$ could be recovered. For pyrogenicity studies, endotoxin was absorbed from the purified material using END-X beads (Associates of Cape Cod, Inc., Woods Hole, Mass.).

9. Pyrogenicity Studies

All studies were preformed on adult male Sprague-Dawley rats (Charles River, UK) of 250–300 g body weight. Rats were individually housed at a temperature between 19°–22° C. Injections were given intracerebroventricularly (icv) via indwelling guide cannulae, stereotaxically implanted in the right lateral ventricle of the brain under general anaesthesia (60 mg/kg sodium pentobarbitone) at least one week prior to the start of the study. Animals were injected (unrestrained) with either MIP-1γ or MIP-1γ at the doses indicated, or with sterile water.

Core temperature was monitored continuously in conscious, undisturbed animals by remote radio-telemetry, via battery-operated biotelemetry transmitters (Data Sciences, St., Paul, Minn.) implanted in the abdominal cavity immediately following implantation of the guide cannula. The output frequency (Hz) of each transmitter was monitored by an antenna mounted in a receiver board situated beneath the cage of each animal and channelled to a peripheral processor (Dataquest III, Data Science, St. Paul, Minn.). Temperatures were sampled at 10 min. intervals. Values are presented as the mean±SEM. Significance was determined through analysis of variance.

10. Assays of Calcium Release in Neutrophils

Bone marrow cells were collected from the femurs of BALB/c mice using Hanks' balanced salt solution (HBSS), supplemented with 10 U of heparin per ml, to flush the marrow cavity. Neutrophils were separated by centrifugation for 30 min at 1000×g over a Ficoll-Hypaque® gradient. After hypotonic lysis of contaminating erythrocytes, the cells were suspended in modified HBSS (supplemented with glucose, 1 mg/ml, and $CaCl_2$, 0.5 mM). Cytosolic calcium ($[Ca^{2+}]_i$) was monitored using the Fura 2/AM (Calbiochem) method (Grynkiewicz et al., 1985).

Neutrophils were loaded with Fura 2/AM as follows. A neutrophil suspension ($10^7$ cells per ml) was incubated at 37° C. with 4 μM Fura 2/AM in modified HBSS to which 0.025% BSA was also added. After 20 min, the cell suspension was diluted by the addition of four volumes of the same medium, lacking Fura 2/AM. The incubation was continued for an additional 30 min.

After loading, the cell suspension was washed twice and resuspended in modified HBSS. $3\times10^6$ cells, suspended in 1.5 ml of medium, were used in each system to assay changes in $[Ca^{2+}]_i$. Fluorescence was recorded using a Perkin-Elner 650 spectrofluorimeter at 335 nm excitation wavelength and 505 nm emission wavelength.

11. Receptor Binding Studies

Purified MIP-1γ and MIP-1α were labelled with $^{125}I$ using the iodogen technique as previously described for the labelling of TNF inhibitor protein (Peppel et al., 1991; 1993; Poltorak et al., 1994). The specific activity of the labeled product was $10^8$ CPM/μg protein. For Scatchard analysis, murine neutrophils, prepared as described above, were suspended at a concentration of $10^7$ cells per ml. 200 μl of each suspension were placed in 1.5 ml Eppendorf tubes. The cells were incubated in the presence of varying concentrations of labelled ligand at 4° C. for one hr while continuously rotated to prevent settling. The incubation was terminated by centrifuging the cell suspension over a cushion of silicone/paraffin oil. The Eppendorf tubes were then snap frozen and the cell pellet cut from the body of the tube for counting.

For displacement assays, neutrophils were incubated in the presence of fixed concentrations of labelled MIP-1α and MIP-1γ, with varying concentrations of unlabelled ligand also present in the system. Binding was allowed to occur for two hr under conditions identical to those above. The same procedure was used to quantitate bound label.

12. Antiserum

A New Zealand white rabbit was bled prior to immunization, and then injected with 0.2 mg of MIP-1γ Freund's complete adjuvant. One month later, the animal was boosted with the injection of 100 μg of antigen in Freund's incomplete antigen. A second boost was given three weeks later, and the animal was bled three days thereafter. The serum thus obtained was used for detection of mouse MIP-1γ in a Western blot assay system (Towbin et al., 1979).

13. Animal Studies

BALB/c mice were maintained in the Animal Resource Center of the University of Texas Southwestern Medical Center (Dallas, Tex.) prior to use in these studies. Mice were sacrificed immediately, or injected with 100 μg of LPS by an intraperitoneal route two hr prior to the harvest of tissues.

B. RESULTS

A total of 66 extinguishable clones were isolated from a screen of 20,000 colonies. These clones were subjected to pilot sequence analysis, using primers positioned at both ends of the insert. The primers used were: 5'-ACAGCTATGACCATG-3' (SEQ ID NO:6) and 5'-GTAAAAGCACGGCCAGT-3' (SEQ ID NO:9). On this basis, 25 clones were recognized immediately. Three of the 25 clones encoded cytokines (lymphotoxin-β, MIP-1α, and thymosin-β4).

Among 41 clones which could not be identified initially, eight were fully sequenced on both strands. Of these, four clones were found to encode homologs of previously identified proteins. One of these coded for MIP-1γ.

The MIP-1γ cDNA initially cloned was not full-length, and therefore, was extended by PCR™ amplification of the library using an internal primer together with a primer hybridizing to a vector sequence located 5' to the insert (5'-ACAGCTATGACCATG-3' [SEQ ID NO:6] and 5'-GTTTCGGTCTATAC-3' [SEQ ID NO:14]). An insert that was 30 base pairs longer was thus obtained and sequenced. It showed the original cDNA to have terminated within the initiation codon, including only the initiator "G". The 5'-untranslated region was found to be 28-nt in length. The total length of the composite cDNA was 1118 nt. No UA-rich element exists within the 714 nt 3'-UTR of the MIP-1γ MRNA. As such, the MIP-1γ MRNA is distinct from most other chemokine mRNAs (FIG. 1).

The MIP-1γ coding sequence specifies a protein of 122 residues. The putative N-terminus of the mature protein is residue +23 with respect to the initiator methionine, based on analogy with known chemokines. A 22-amino acid propeptide sequence is present, and contains a hydrophobic element which would be predicted to cause efficient secretion of the translation product. In its processed form, MIP-1γ is expected to be 100 amino acids in length. A computer-based alignment and analysis of homology among C-C chemokine family members assigns C10 as the closest relative of MIP-1γ (45% identity at the amino acid level), and MIP-1α and MIP-1β (24% and 20% identity at the amino acid level, respectively) as the next closest relatives. The alignment was achieved using the Clustal V program with a fixed gap penalty 10 and floating gap penalty 10 and weighted parameters.

Figure 2A:
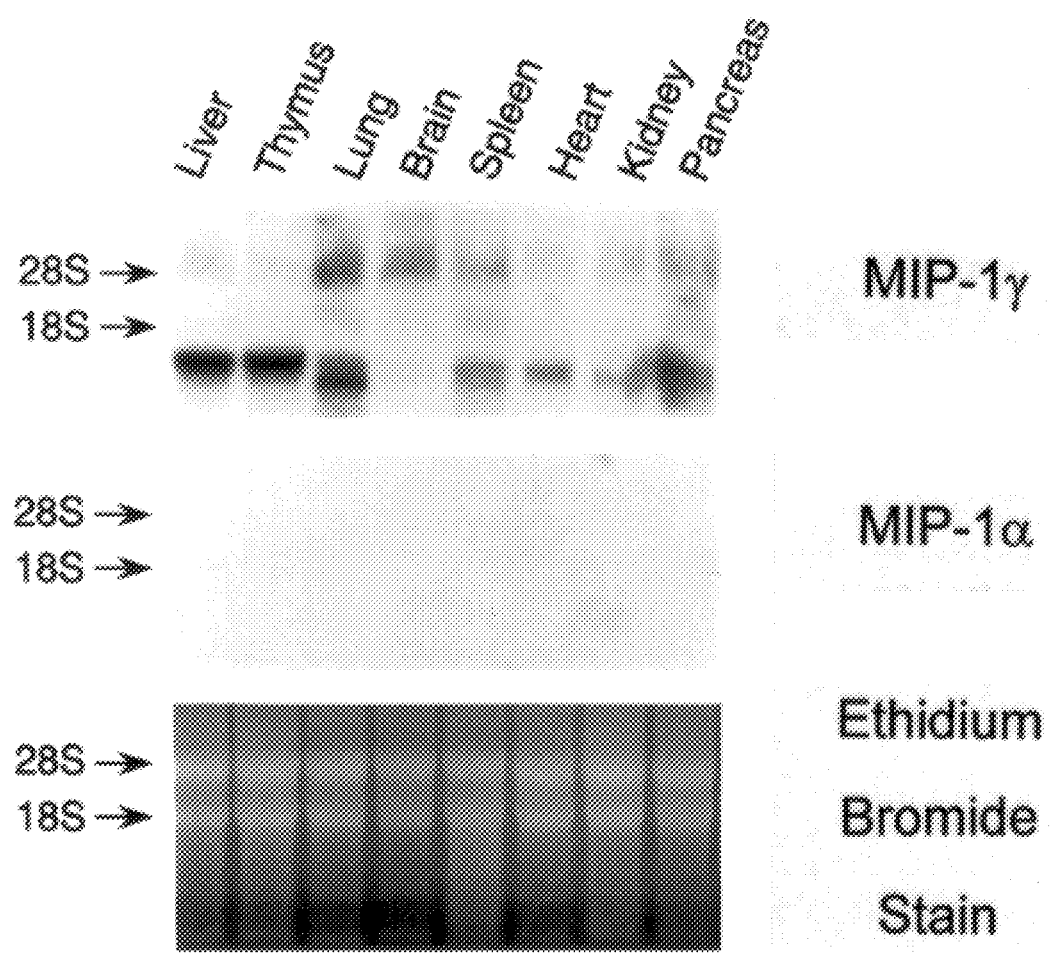
FIG. 2A. Expression of MIP-1γ MRNA in the tissues of a normal mouse, and in the tissues of a mouse injected intraperitoneally with 200 μg of LPS four hr prior to sacrifice. Top panel illustrates MRNA probed for MIP-1γ. Bottom panel illustrates the ethidium bromide-stained RNA on nylon membranes. The location of 28S and 18S ribosomal bands is indicated by arrows.
Figure 2B:
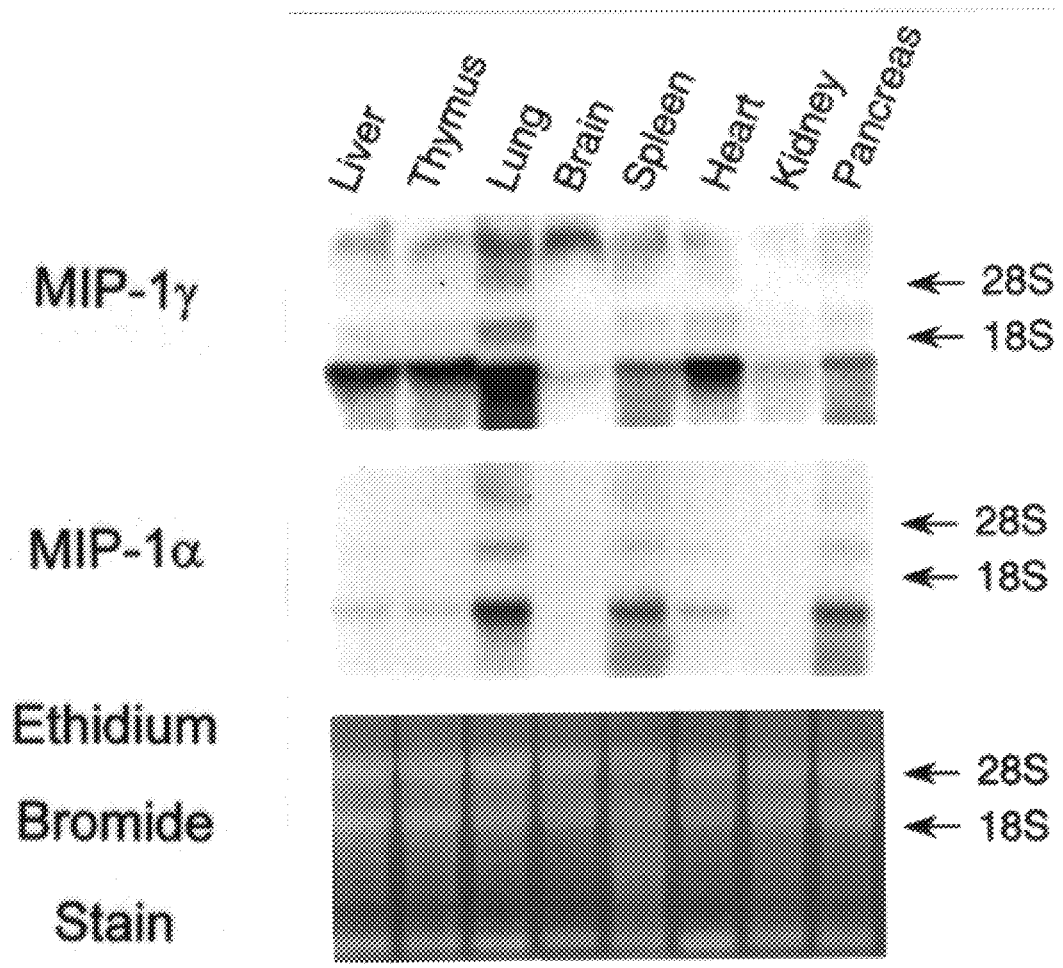
FIG. 2B. Expression of MIP-1α mRNA in the tissues of a normal mouse, and in the tissues of a mouse injected intraperitoneally with 200 μg of LPS four hr prior to sacrifice. Top panel illustrates mRNA probed for MIP-1α. Bottom panel illustrates the ethidium bromide-stained RNA on nylon membranes. The location of 28S and 18S ribosomal bands is indicated by arrows.

MIP-1γ may be identified in most tissues of normal mice. Cs-purified RNA obtained from several organs of normal and LPS-treated mice was subjected to electrophoresis and Northern blot analysis. The major sites of mRNA expression in normal mice were the liver, the lung, and the thymus, although some transcript was detected in all tissues examined except brain (FIG. 2A and FIG. 2B). In LPS-injected mice, net induction of expression was noted only in the heart and lungs, but in no other tissue. When the blots were reprobed for MIP-1γ and MIP-1α are subject to very different regulatory mechanisms. The former is constitutively expressed, and the latter is highly inducible.

Figure 3:
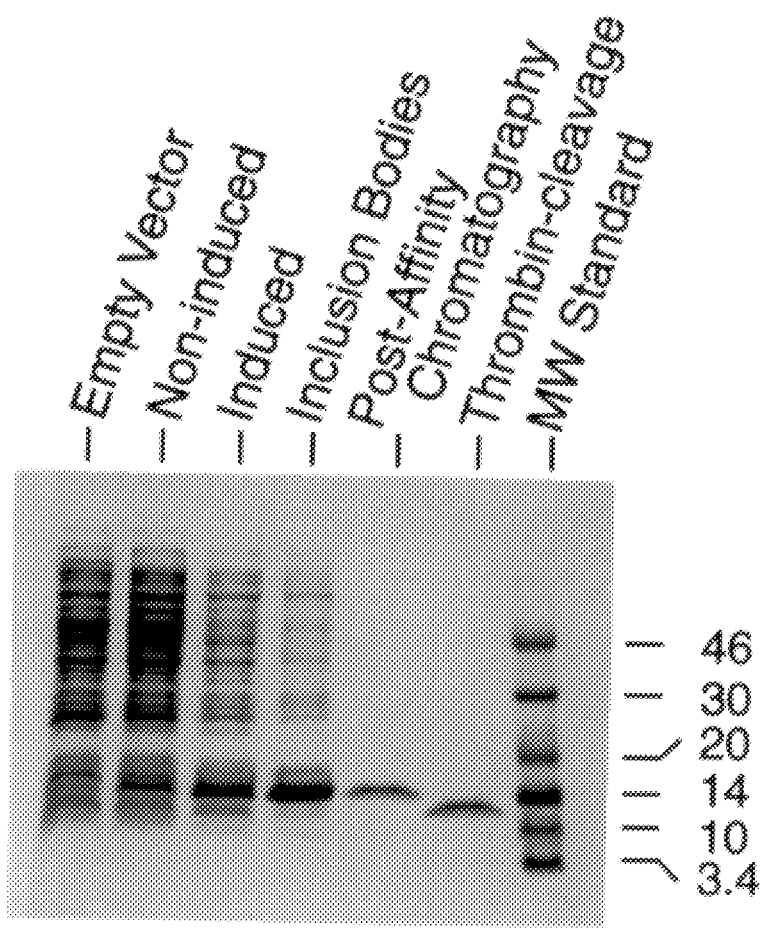
FIG. 3. Purified recombinant MIP-1γ, produced as a histidine-tagged fusion protein in *E. coli*. Lysates were prepared from bacteria transfected with an empty expression vector, or from bacteria transfected with the MIP-1γ expression construct. Various steps in purification are indicated. Gel was stained with coomassie blue.

A histidine-tagged fusion protein was created, and purified using a nickel-agarose affinity column. The purified protein was cleaved using thrombin to yield a 10 kDa product (FIG. 3), which remained soluble in 0.1M phosphate buffer, pH 7.8.

Figure 4:
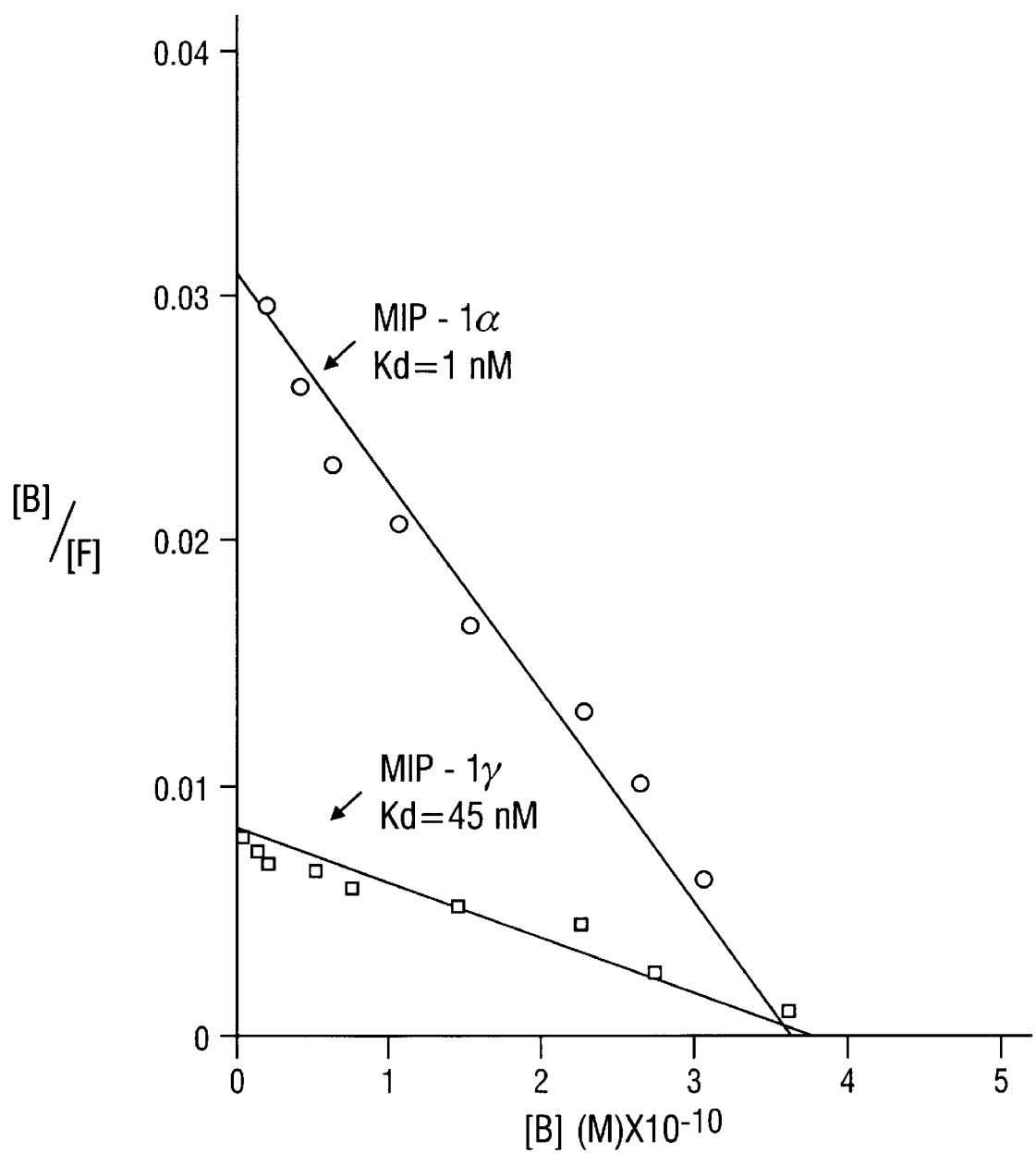
FIG. 4. Scatchard Analysis of MIP-1γ and MIP-1α binding to neutrophils $K_d$ for each curve as indicated. Methods described in the text.
Figure 5A:
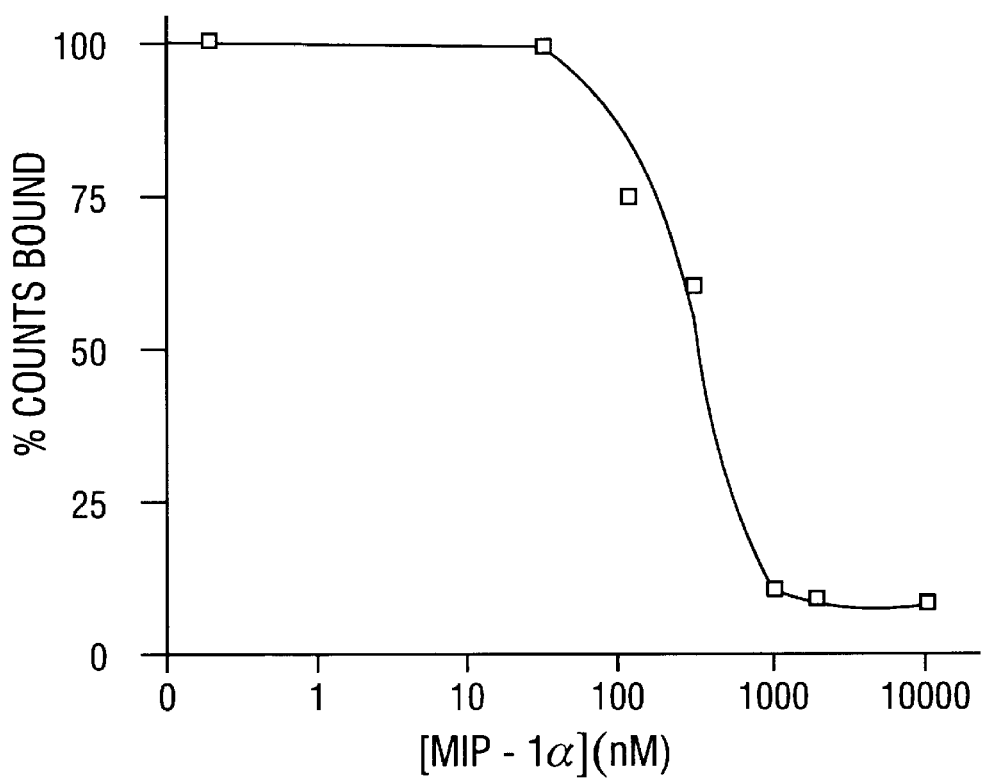
FIG. 5A. Receptor competition: displacement of MIP-1α by MIP-1α. Methods are described in Example 1.
Figure 5B:
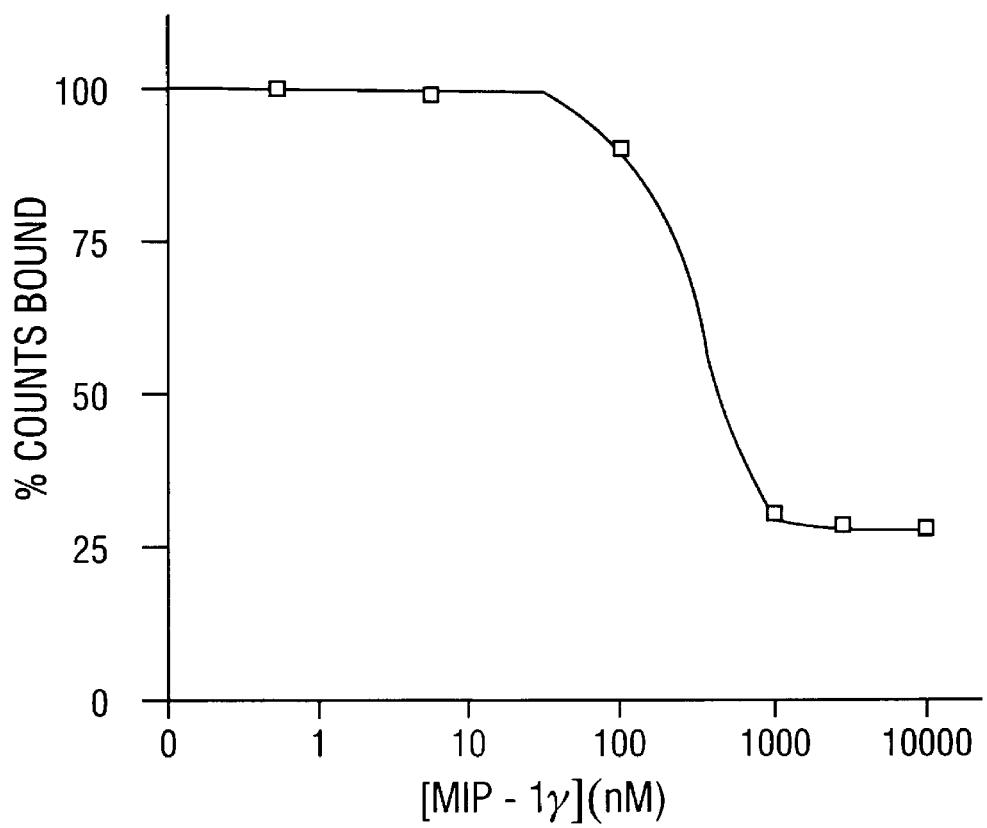
FIG. 5B. Receptor competition: displacement of MIP-1α by MIP-1γ. Methods are described in Example 1.
Figure 5C:
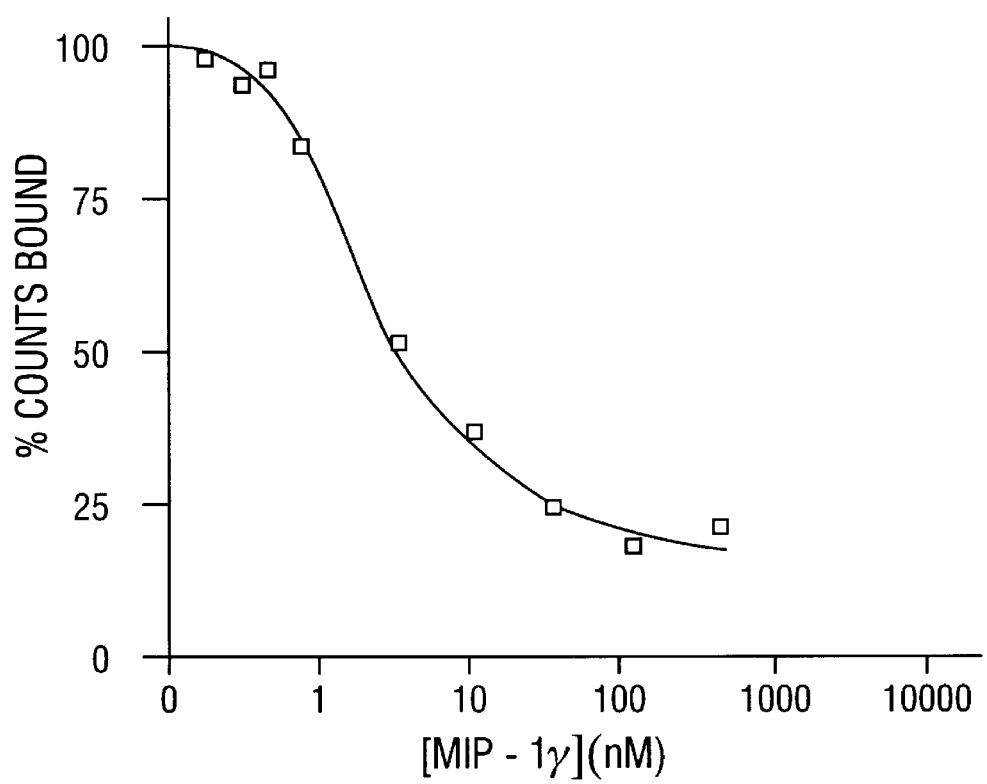
FIG. 5C. Receptor competition: displacement of MIP-1γ by MIP-1γ. Methods are described in Example 1.
Figure 5D:
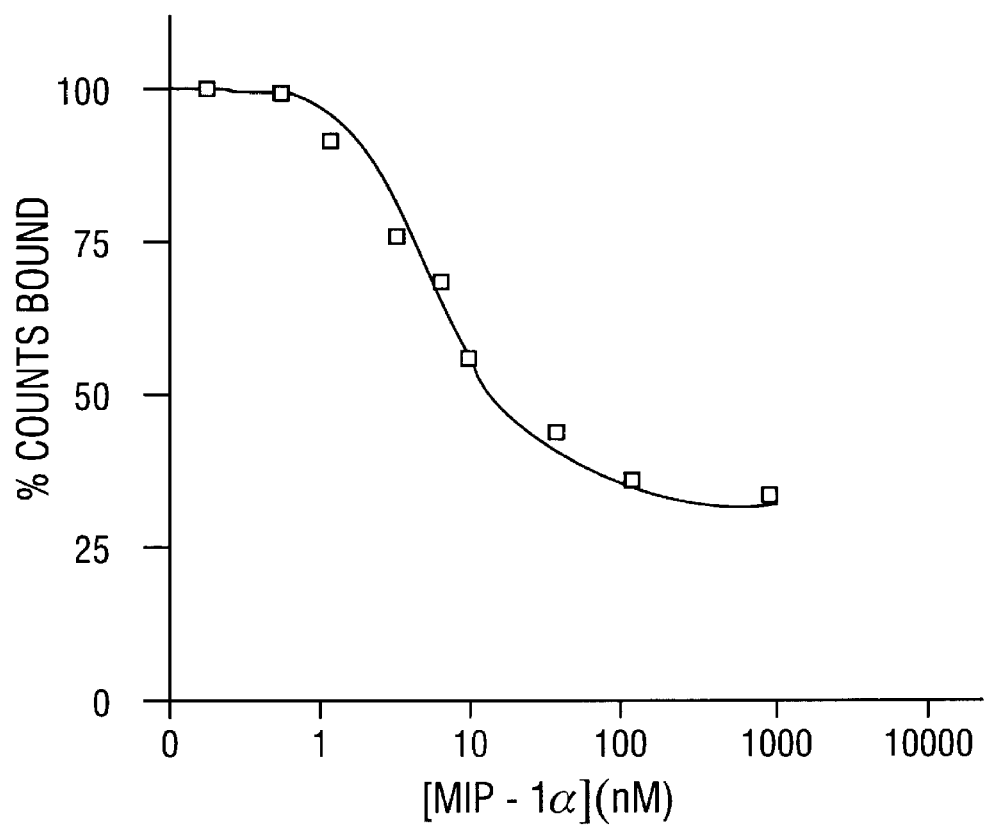
FIG. 5D. Receptor competition: displacement of MIP-1γ by MIP-1α. Methods are described in Example 1.

Radiolabeled MIP-1γ was found to bind with high affinity to a receptor on the surface of NIH 3T3 cells and murine neutrophils. In the latter case, Scatchard analysis revealed a dissociation constant ($K_d$) of approximately 45 nM. On mouse neutrophils, the receptor was present at a mean density of $2.1 \times 10^4$ binding sites per cell, assuming a monomeric ligand. The receptor for MIP-1α was present at approximately the same density, but bound the ligand with a $K_d$ of 10 nM (FIG. 4).

When unlabeled MIP-1γ was used to compete for binding by labelled MIP-1α, or conversely, when unlabelled MIP-1α was used to compete for binding by labelled MIP-1γ, it was apparent that greater than 90% of the binding sites were shared (FIG. 5A, FIG. 5B, FIG. 5C, and FIG. 5D). These data suggest that the two ligands do, in fact, occupy a common receptor.

Figure 6:
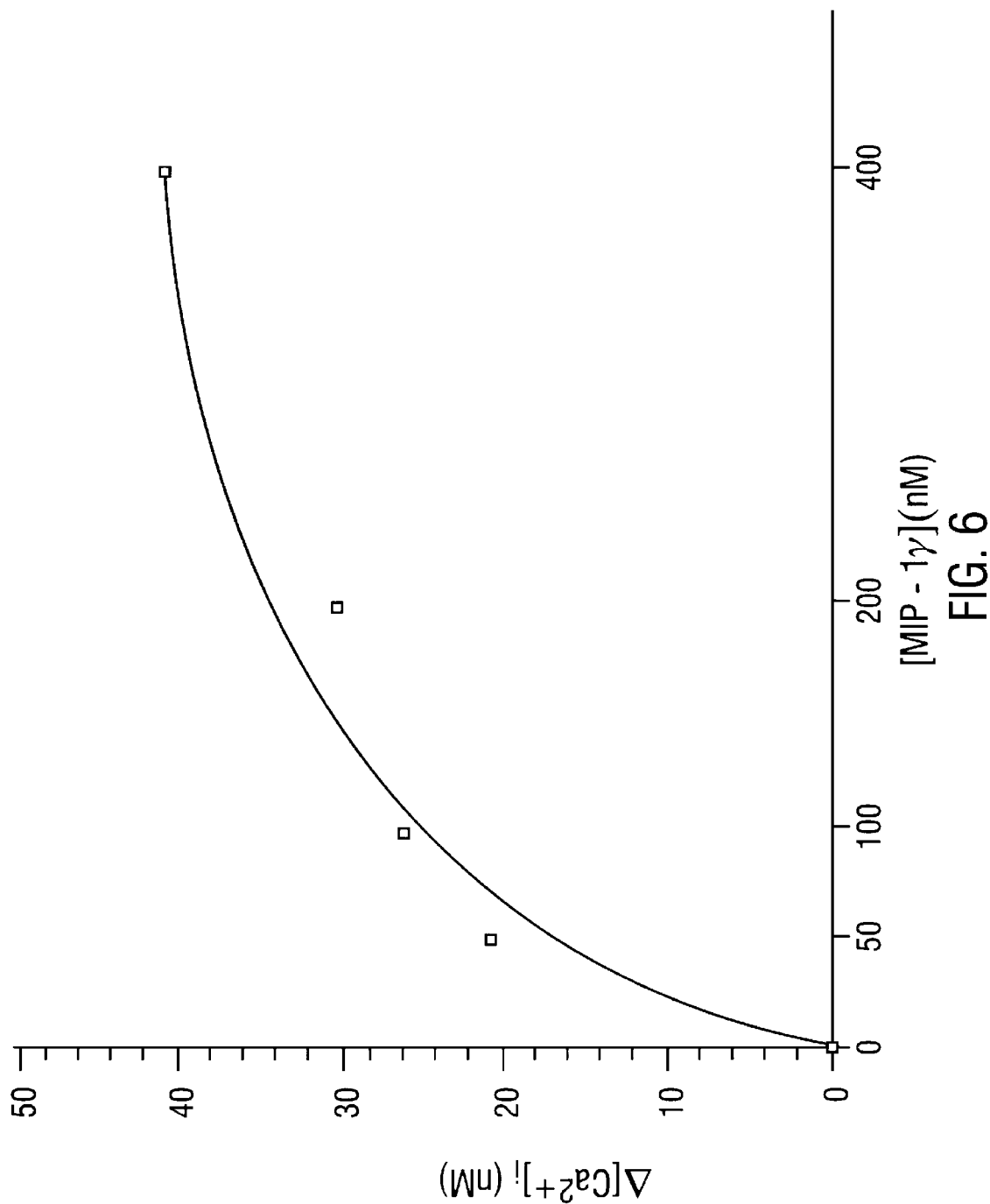
FIG. 6. Release of intracellular calcium stores in neutrophils, triggered by MIP-1γ and MIP-1α. Shown is the dose-response curve for MIP-1γ.

In order to determine whether MIP-1α and MIP-1γ exerted common signals, the effect of MIP-1γ on calcium flux in neutrophils was examined. At concentrations as low as 50 nM, MIP-1γ caused a transient increase in cytosolic calcium concentration, occurring within a few seconds after addition of the protein to a neutrophil suspension (FIG. 6). A maximum response was detected with the use of 400 nM MIP-1γ.

Figure 7:
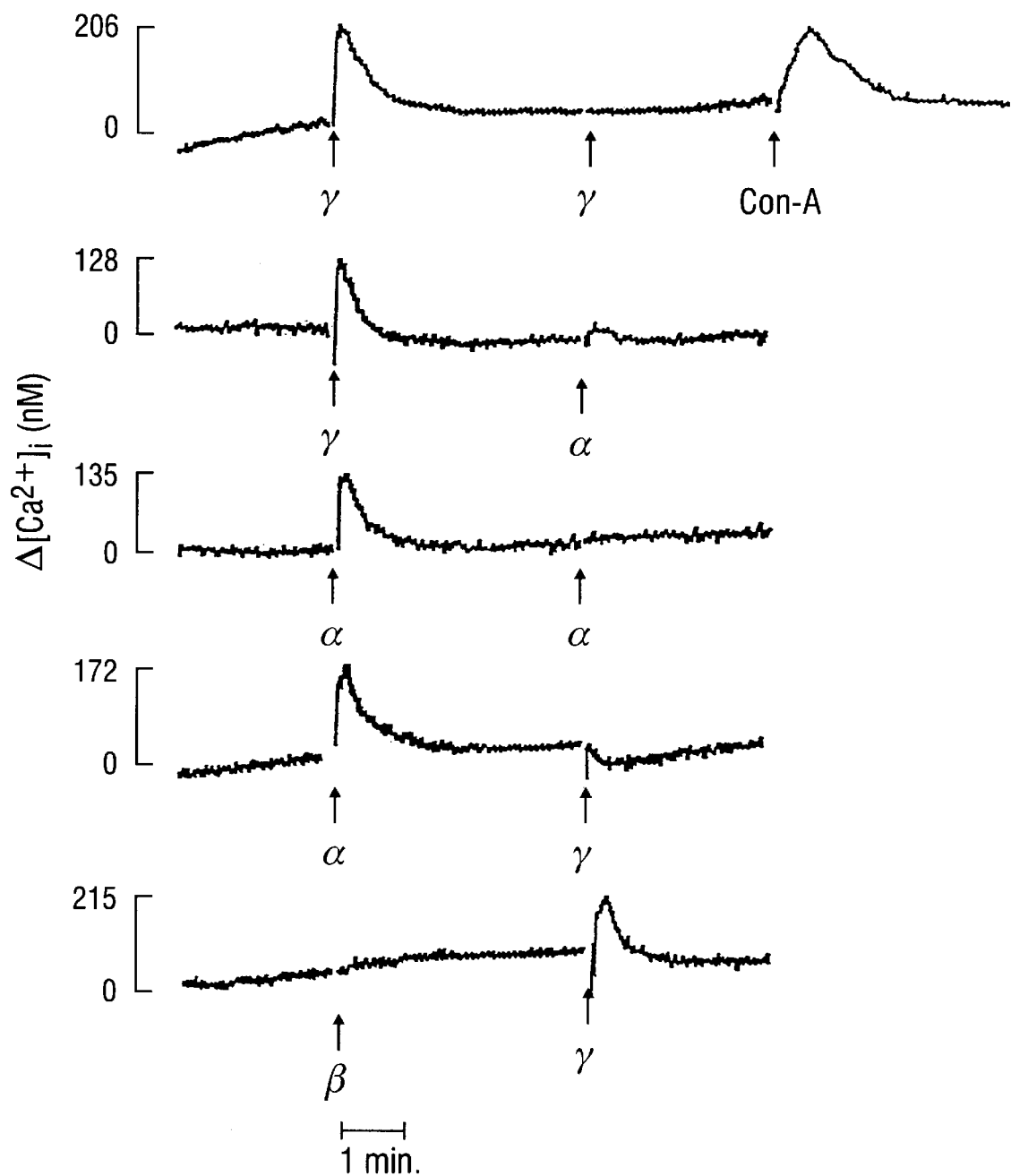
FIG. 7. Release of intracellular calcium stores in neutrophils, triggered by MIP-1γ and MIP-1α. Shown is the attenuation of chemokine response in double-stimulation test. Chemokines used in these tests (MIP-1α, 200 nM; MIP-1β, 167 nM; and MIP-1γ 500 nM) as well as concanavalin A 300 μg/ml, are indicated with arrows. Scale indicates the calculated change in intracellular $Ca^{++}$ observed in response to each primary chemokine stimulus.

While neutrophils responded promptly to the addition of either MIP-1α or MIP-1γ with a rise in cytosolic calcium, a second challenge with either cytokine failed to elicit a response (FIG. 7). However, concanavalin-A was able to stimulate the cells after MIP treatment (top tracing, FIG. 7), indicating that the cells remained viable, and capable of releasing further calcium after MIP treatment. It may be concluded that the MIPs utilize a common signal transduction pathway, as each is capable of eliciting desensitization, both to itself and to its homolog.

Figure 8A:
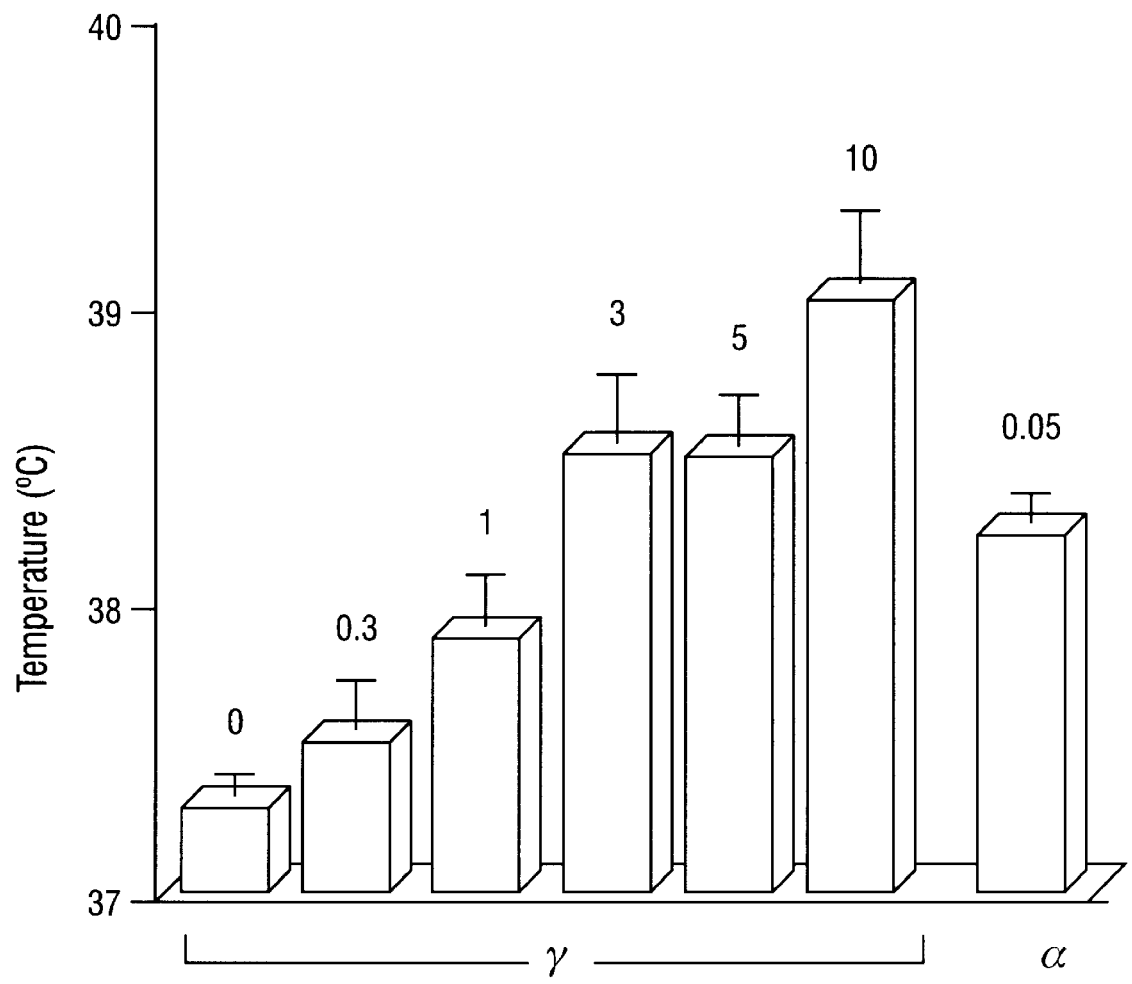
FIG. 8A. Pyrogenicity of MIP-1γ in rats. Shown is the dose-response curve indicting the mean core body temperature of rats six hr after icv injection with MIP-1γ or MIP-1α at the indicated dose (μg). Error bars indicate standard error (n=4 animals per group).
Figure 8B:
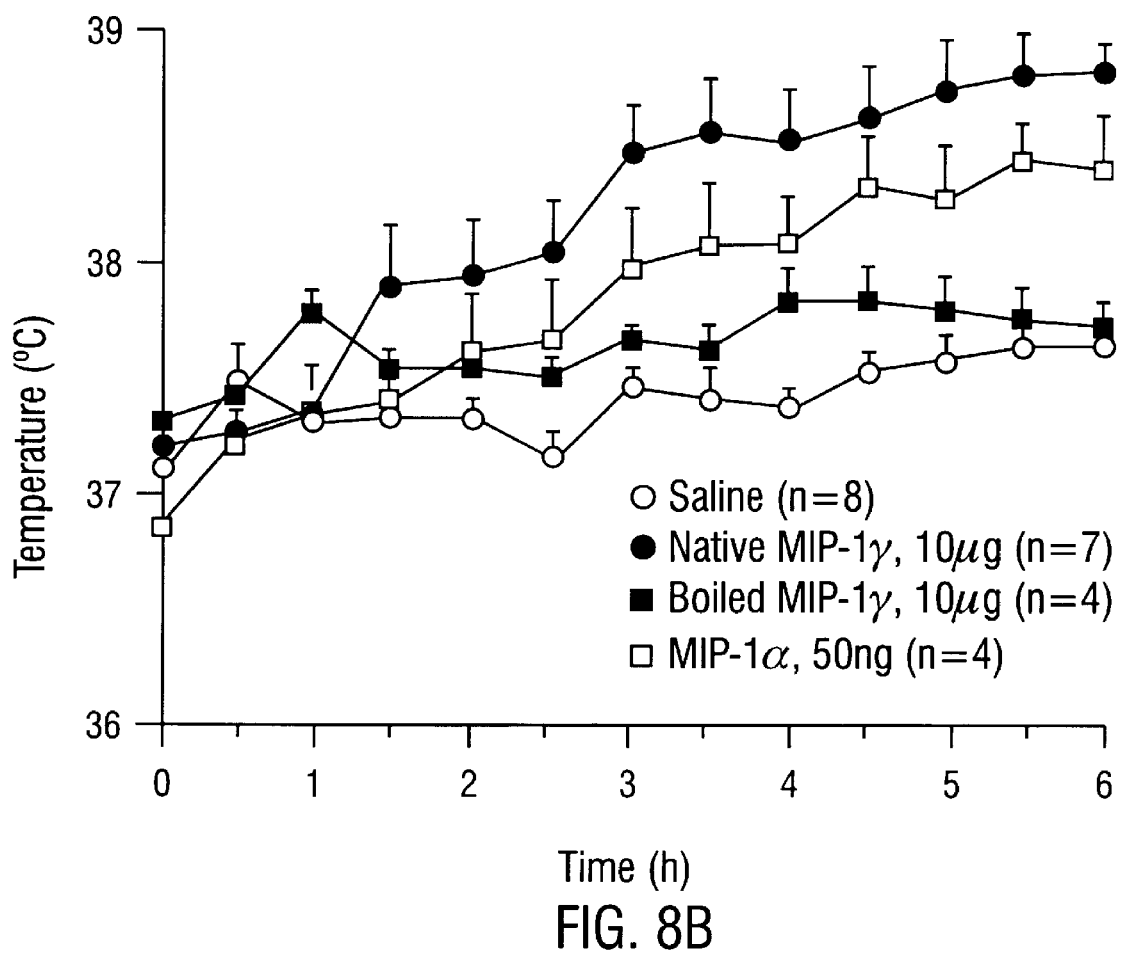
FIG. 8B. Pyrogenicity of MIP-1γ in rats. Shown are the fever curves of rats injected by an icv route with saline (sal), MIP-1γ, heat-inactivated MIP-1γ, or MIP-1α as indicated (inset). Error bars indicated standard error; n denoted for each curve in inset.

Fever is a common biological response to many cytokines (Beutler et al., 1994), including members of the MIP-1 group (Myers et al., 1993; Zawada et al., 1993), and is believed to result from a direct action of cytokines in the brain (probably within the hypothalamus), leading to alteration of the "set point" of body temperature. The nature of chemokine receptors within the brain, and their relationship to leukocyte chemokine receptors, has not been defined. In order to determine whether MIP-1γ elicits fever as well as neutrophil activation, the protein was administered by either systemic or intracerebroventricular (icv) routes. Intravenous administration of MIP-1γ to mice at a dose of 1 mg/animal did not cause evident febrile or toxic reactions. In rats, however, icv administration of non-denatured recombinant MIP-1γ promptly induced fever, whereas the administration of heat-inactivated MIP-1γ did not. Therefore, MIP-1γ, like MIP-1α, appears to be pyrogenic. With respect to the preparations used, MIP-1α was substantially more potent (FIG. 8A and FIG. 8B).

Figure 9:
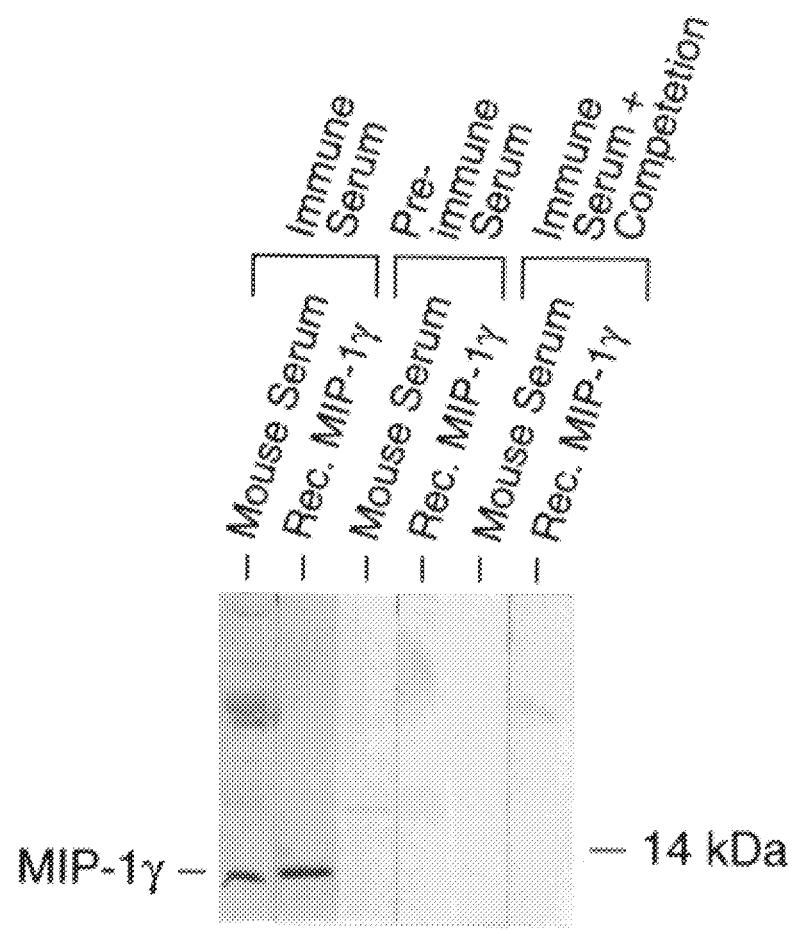
FIG. 9. Detection of MIP-1γ in the serum of a normal mouse by immunoblot analysis. 1.0 μl of serum was added the gel, alternating with 1 ng of thrombin-cleaved recombinant MIP-1γ used as a standard. After transfer to nitrocellulose, blots were developed using antiserum against MIP-1γ, pre-immune serum from the same rabbit, or antiserum against MIP-1γ that had been pre-absorbed with 10 μg of recombinant protein (immune serum+competition). Each of these detecting reagents was diluted 1:100 for use. 1 ng of recombinant MIP-1γ stains with an intensity approximately equal to that of the MIP-1γ present in normal serum; hence, normal serum contains MIP-1γ at a concentration of approximately 1 μg/ml. This observation was confirmed in five additional animals.

Surprisingly, in view of its neutrophil-activating and pyrogenic effects, MIP-1γ circulates in the plasma of normal mice at a concentration of approximately 1 μg/ml, and is easily detected on Western blot. As demonstrated in FIG. 9, pre-immune serum from an animal immunized against MIP-1γ is non-reactive with proteins in the plasma of a normal mouse, whereas immune serum reacts strongly with a single species of $M_r$=10 kDa, similar in size to the cleaved recombinant protein. Reactivity is lost when the immune serum is preabsorbed with an excess of the recombinant protein. Vastly larger amounts of the protein are found in tissue homogenates taken from normal mice suggesting that constitutive extravascular production of the protein may account for its presence in blood, and that the concentration of MIP-1γ in interstitial fluid surrounding cells of the heart, spleen, liver, and other tissues is extremely high.

EXAMPLE 2

PROPHYLAXIS OF SEPSIS IN A MURINE MODEL: MIP-1γ ENHANCES SURVIVAL DURING LPS CHALLENGE

FIG. 10 shows a Kaplan-Meier plot of mouse survival following administration of lipopolysaccharide (LPS) with or without concurrent treatment with MIP-1γ. Mice (10 in each group) were injected intravenously with 80 μg of recombinant MIP-1γ in saline, or with saline alone. All mice were injected intraperitoneally with 150 μg of E. coli LPS (isolated from strain 0127:B8) which was obtained from Difco Laboratories (Detroit, Mich.) immediately afterwards.

A significant enhancement of survival was demonstrated in mice that received MIP-1γ treatment. Of the 10 mice receiving LPS alone, 5 died within 2 days. In sharp contrast, all of the mice receiving concurrent MIP-1γ injections survived the LPS septic challenge.

The "discharge" of the chemokine receptors engaged by MIP-1γ occurring out of the normal temporal sequence that occurs in endotoxic shock may render them refractory to stimulation by endovenously produced chemokines, and thereby protect against injurious effects that they normally render. MIP-1γ present in vivo at supernormal concentrations may also stimulate the production of factors that are protective in endotoxic shock. In either event, it is clear that MIP-1γ is an effective means of countering endotoxicity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text:

U.S. Pat. No. 3,791,932.
U.S. Pat. No. 3,949,064.
U.S. Pat. No. 4,196,265.
U.S. Pat. No. 4,174,384.
U.S. Pat. No. 4,489,555.

U.S. Pat. No. 4,554,101.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 4,683,195.
U.S. Pat. No. 4,683,202.
U.S. Pat. No. 4,965,188.
U.S. Pat. No. 5,168,050.
U.S. Pat. No. 5,176,995.
Ahuja et al., "Molecular piracy of mammalian interleukin-8 receptor type B by herpesvirus saimiri," *J. Biol. Chem.* 268:20691–20694, 1993
Ahuja et al., *Immunol. Today,* 15:281, 1994.
Allen and Choun,"Large unilamellar liposomes with low uptake into the reticuloendothelial system," *FEBS Lett.,* 223:42–46, 1987.
Altschul, Stephen F. et al., "Basic local alignment search tool," *J. Mol. Biol.,* 215:403–410, 1990.
Baker, N. E. et al., "Nucleotide sequence of the human melanoma growth stimulatory activity (MGSA) gene," *Nucl. Acids Res.* 18:6453, 1990.
Beutler, In: *Cecil Textbook of Medicine,* Wyngaarden, Jr., Smith, Bennett, Eds., W. B. Saunders Company, Philadelphia, pp. 1568–1571, 1994.
Bischoff et al., *Eur. J. Immunol.,* 23:761–767, 1993.
Boshart et al., *Cell,* 66:849–859, 1991.
Broxmeyer et al., *Blood,* 76:1110–1116, 1990.
Broxmeyer et al., *J. Immunol.,* 150:3448–3458, 1993.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.
Caput et al., *Proc. Natl. Acad. Sci. USA,* 83:1670–1674, 1986.
Church, G. M. et al., *Proc. Natl. Acad. Sci. USA,* 81:1991–1995.
Couvreur, "Polyalkyleyanoacrylates as colloidal drug carriers," *Crit. Rev. Ther. Drug Carrier Syst.,* 5:1–20, 1988.
Couvreur et al., "Nanocapsules, a new lysosomotropic carrier," *FEBS Lett.,* 84:323–326, 1977.
Davatelis et al., *J. Exp. Med.,* 167:1939–1944, 1988.
Desiderio and Campbell, "Liposome-encapsulated cephalotin in the treatment of experimental murine-salmonellosis," *J. Reticuloendothel. Soc.,* 34:279–287, 1983.
Gabizon and Papahadjopoulos, "Liposomes formulations with prolonged circulation time in blood and enhanced uptake by tumors," *Proc. Natl. Acad. Sci. USA,* 85:6949–6953, 1988.
Gefter et al., *Somatic Cell Genet.,* 3:231–236, 1977.
Goding, "Monoclonal Antibodies: Principles and Practice," pp. 60–74. 2nd Edition, Academic Press, Orlando, Fla., 1986.
Grynkiewicz et al., *J. Biol. Chem.,* 260:340, 1985.
Hannum et al., *Nature,* 343:336, 1990.
Harlow, E. and Lane, D., "Antibodies: a Laboratory Manual," Cold Spring Harbor Laboratory, Cold Spring Harbor, N.Y. 1988.
Henry-Michelland et al., "Attachment of antibiotics to nanoparticles; Preparation, drug-release and antimicrobial activity in vitro, *Int. J. Pharm.,* 35:121–127, 1987.
Horuk et al., *Biochemistry,* 32:5733–5738, 1993.
Horuk et al., *Immunol. Today,* 15;169, 1994.
Horuk et al., *Science,* 261:1182–1184, 1993.
Jameson and Wolf, *Compu. Appl. Biosci.,* 4(1):181–6, 1988.
Kelvin et al., *J. Leuk. Biol.,* 54:604, 1993.
Killary and Fournier, *Cell,* 38:523–534, 1984.
Kohler and Milstein, *Eur. J. Immunol.,* 6:511–519, 1976.
Kohler and Milstein, *Nature,* 256:495–497, 1975.
Kruys et al., *Enzyme,* 44:193–202, 1993.
Kruys et al., *Gene,* 72:191–200, 1988.
Kruys et al., *J. Exp. Med.,* 177:1383–1390, 1993.
Kruys et al., *Proc. Natl. Acad. Sci.,* 84:6030–6034, 1987.
Kruys et al., *Science,* 245:852–855, 1989.
Kuby, J., *"Immunology"* 2nd Edition. W. H. Freeman & Company, New York, 1994.
Kuna et al., *J. Immunol.,* 150:1932–1943, 1993.
Kyte, J., and Doolittle, R. F., *J. Mol. Biol.* 157(1):105–132, 1982.
Laemmli, *Nature,* 227:680, 1970.
Maloy, S. R., "Experimental Techniques in Bacterial Genetics", Jones and Bartlett Publishers, Boston, Mass. 1990.
Maloy, et al., "Microbial Genetics" 2nd Edition. Jones and Bartlett Publishers, Boston, Mass., 1994.
Maniatis et al., "Molecular Cloning: a Laboratory Manual," Cold Spring Harbor Laboratory, Cold Spring Harbor, N.Y., 1982.
McColl et al., *J. Immunol.,* 150:4550, 1993.
Myers et al., *Neurochem. Res.,* 18:667–673, 1993.
Neote et al., *Blood,* 84:44, 1994.
Neote et al., *Cell,* 72:415–425, 1993.
Neote et al., *J. Biol. Chem.,* 268:12247–12249, 1993.
Oppenheim et al., *Ann. Rev. Immunol.,* 9:617, 1991.
Pearson, W. R. et al., *Proc. Natl. Acad. Sci. USA,* 85:2444–2448, 1988.
Peppel et al., *J. Exp. Med.,* 174:1483, 1991; 1993.
Peppel et al., *J. Immunol.,* 151:5699, 1991; 1993.
Petit et al., *Proc. Natl. Acad. Sci. USA,* 83:2561–2565, 1986.
Poltorak et al., *J. Immunol. Methods,* 169:93, 1994.
Prokop, A., and Bajpai, R. K., "Recombinant DNA Technology I" *Ann. N.Y. Acad. Sci.,* Vol. 646, 1991.
Ralph, P., *Lymphokine & Cytokine Res.,* 10:237–237, 1991.
Richmond, A. et al., "Extraction of a melanoma growth-stimulatory activity from culture medium conditioned by the Hs-0294 human melanoma cell line," *Cancer Res.,* 43:2106–2112, 1983.
Richmond, A. et al., "Characterization of autostimulatory and transforming growth factors from human melanoma cells," *Cancer Res.,* 45:6390–6394, 1985.
Richmond, A. et al., "Purification of melanoma growth stimulatory activity," *J. Cell. Physiol.,* 129:375–384, 1986.
Rot et al., *J. Exper. Med.,* 176:1489–1495, 1992.
Ruppert et al., *Cell,* 61:895–904, 1990.
Sambrook et al., "Molecular Cloning: A Laboratory Manual," 2nd Edition; Cold Spring Harbor Laboratory, Cold Spring Harbor, N.Y., 1989.
Schall et al., *J. Exper. Med.,* 177:1821–1826, 1993.
Schall, T. J., Cytokine, 3:165–183, 1991.
Segal, I. H., "Biochemical Calculations" 2nd Edition. John Wiley and Sons, New York, 1976.
Spoerel, *Methods Enzymol.* 152:588–597, 1987.
Thomas, H. G. et al., "High yield purification of melanoma growth stimulatory activity," *Molec. Cell. Endocrin.,* 57:69–76, 1988.
Towbin et al., *Proc. Natl. Acad. Sci., USA,* 76:4350, 1979.

Wang et al., *J. Exp. Med.,* 177:699, 1993.
Wang et al., *J. Immunol.,* 150:3022, 1993.
Wolf et al., *Compu. Appl. Biosci.,* 4(1):187–91, 1988.
Wolpe et al., *J. Exp. Med.,* 167:570–581, 1988.
Young and Davis, "Efficient Isolation of Genes by Using Antibody Probes," *Proc. Natl. Acad. Sci. USA,* 80:1194–1198, 1983.
Zawada et al., *Brain Res. Bull.,* 32:17–21, 1993.

What is claimed is:

1. An isolated DNA segment that encodes a polypeptide having the sequence of SEQ ID NO:2 or the complement of said DNA segment.

2. The DNA segment of claim 1 that encodes a murine MIP-1γ protein.

3. The DNA segment of claim 1, comprising a mip-1γ gene that includes at least a 30 nucleotide contiguous nucleic acid sequence from between positions 29 and position 397 of SEQ ID NO:1.

4. The DNA segment of claim 1, comprising a MIP-1γ gene that encodes a MIP-1γ peptide of about 122 amino acids in length.

5. The DNA segment of claim 1, comprising a mip-1γ gene that includes the contiguous nucleic acid sequence from position 29 to position 397 of SEQ ID NO:1.

6. The DNA segment of claim 1, positioned under the control of a promoter.

7. The DNA segment of claim 6, positioned under the control of a recombinant promoter.

8. The DNA segment of claim 1, further defined as a recombinant vector.

9. An isolated nucleic acid segment characterized as:
   (a) A nucleic acid segment comprising a sequence that consists of at least 30 contiguous nucleotides that have the same sequence as, or are complementary to, 30 contiguous nucleotides of SEQ ID NO:1; or,
   (b) a nucleic acid segment of from 14 to about 769 nucleotides in length that hybridizes to the nucleic acid segment of SEQ ID NO:1 between positions 1–188 or 349–1118, or the complement thereof, under hybridization conditions of high stringency.

10. The nucleic acid segment of claim 9 wherein the segment comprises a sequence region of at least 30 contiguous nucleotides from SEQ ID NO:1, or the complement thereof.

11. The nucleic acid segment of claim 9 wherein the segment comprises a sequence region of at least about 30 nucleotides; or wherein the segment is about 30 nucleotides in length.

12. The nucleic acid segment of claim 11, wherein the segment comprises a sequence region of at least about 30 nucleotides; or wherein the segment is about 30 nucleotides in length.

13. The nucleic acid segment of claim 12, wherein the segment comprises a sequence region of at least about 50 nucleotides; or wherein the segment is about 50 nucleotides in length.

14. The nucleic acid segment of claim 13, wherein the segment comprises a sequence region of at least about 100 nucleotides; or wherein the segment is about 100 nucleotides in length.

15. The nucleic acid segment of claim 14, wherein the segment comprises a sequence region of at least about 200 nucleotides; or wherein the segment is about 200 nucleotides in length.

16. The nucleic acid segment of claim 15, wherein the segment comprises a sequence region of at least about 500 nucleotides; or wherein the segment is about 500 nucleotides in length.

17. The nucleic acid segment of claim 16, wherein the segment comprises a sequence region of at least about 1000 nucleotides; or wherein the segment is about 1000 nucleotides in length.

18. The nucleic acid segment of claim 16, wherein the segment comprises a sequence region of about 1118 nucleotides; or wherein the segment is about 1118 nucleotides in length.

19. The nucleic acid segment of claim 9, wherein the segment is up to 10,000 basepairs in length.

20. The nucleic acid segment of claim 19, wherein the segment is up to 5,000 basepairs in length.

21. The nucleic acid segment of claim 20, wherein the segment is up to 3,000 basepairs in length.

22. The nucleic acid segment of claim 21, wherein the segment is up to 1,000 basepairs in length.

23. The nucleic acid segment of claim 9, further defined as a DNA segment.

24. The nucleic acid segment of claim 9, further defined as a RNA segment.

25. A recombinant host cell comprising a DNA segment as defined in claim 9.

26. The recombinant host cell of claim 25, wherein the DNA segment is introduced into the cell by means of a recombinant vector.

27. The recombinant host cell of claim 25, wherein the whole cell expresses the DNA segment to produce the encoded MIP-1γ protein or peptide wherein said protein or peptide has the amino acid sequence of SEQ ID NO:2.

28. The recombinant host cell of claim 25, further defined as a bacterial host cell.

29. The recombinant host cell of claim 28, wherein the bacterial host cell is *E. coli*.

30. A method of using a DNA segment that includes an isolated mip-1γ gene, comprising the steps of:
   (a) preparing a recombinant vector in which a MIP-1γ encoding DNA segment is positioned under the control of a promoter wherein said MIP-1γ has the sequence of SEQ ID NO:2;
   (b) introducing said recombinant vector into recombinant host cell;
   (c) culturing a recombinant host cell under conditions effective to allow expression of the encoded MIP-1γ protein or peptide; and,
   (d) collecting said expressed MIP-1γ protein or peptide.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 1118 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 29..394

(xi) SEQUENCE DESCRIPTION: SEQ ID NO:1:

```
GGGCCAGCTG GGTCTGCCCA CTAAGAAG ATG AAG CCT TTT CAT ACT GCC CTC                52
                                Met Lys Pro Phe His Thr Ala Leu
                                 1               5

TCC TTC CTC ATT CTT ACA ACT GCT CTT GGA ATC TGG GCC CAG ATC ACA              100
Ser Phe Leu Ile Leu Thr Thr Ala Leu Gly Ile Trp Ala Gln Ile Thr
        10              15                  20

CAT GCA ACA GAG ACA AAA GAA GTC CAG AGC AGT CTG AAG GCA CAG CAA              148
His Ala Thr Glu Thr Lys Glu Val Gln Ser Ser Leu Lys Ala Gln Gln
 25              30                  35                      40

GGG CTT GAA ATT GAA ATG TTT CAC ATG GGC TTT CAA GAC TCT TCA GAT              196
Gly Leu Glu Ile Glu Met Phe His Met Gly Phe Gln Asp Ser Ser Asp
                    45                  50                  55

TGC TGC CTG TCC TAT AAC TCA CGG ATT CAG TGT TCA AGA TTT ATA GGT              244
Cys Cys Leu Ser Tyr Asn Ser Arg Ile Gln Cys Ser Arg Phe Ile Gly
            60                  65                  70

TAT TTT CCC ACC AGT GGT GGG TGT ACC AGG CCG GGC ATC ATC TTT ATC              292
Tyr Phe Pro Thr Ser Gly Gly Cys Thr Arg Pro Gly Ile Ile Phe Ile
        75                  80                  85

AGC AAG AGG GGG TTC CAG GTC TGT GCC AAC CCC AGT GAT CGG AGA GTT              340
Ser Lys Arg Gly Phe Gln Val Cys Ala Asn Pro Ser Asp Arg Arg Val
        90                  95                  100

CAG AGA TGC ATT GAA AGA TTG GAG AAA AAC TCA CAA CCA CGG ACC TAC              388
Gln Arg Cys Ile Glu Arg Leu Glu Lys Asn Ser Gln Pro Arg Thr Tyr
105             110                 115                 120

AAA CAA TAACATTTGC TTTAGAGAAG GGTGTGAACT GCCAGCTACT TTCTTTGGTC               444
Lys Gln

TTCCCCAGTG ACCACCTAAG TGGCTCTAAG TGTTTATTTT TATAGGTATA TAAACATTTT            504

TTTTTTCTGT TTCCACTTTA AAGTGGCATA TCTGGCTTTG TCACAGAGGG GAAACTTGTC            564

TGTGCCAACC CCAGTCATCT GAAAACTCAG ATGCCTGGGA AGGTCTGAAG CTGACCTCAA            624

TGACTACACA TAATATTTGA TTGAGATAAA TGGGCAAGGT CTGGAGAGAT GGCTTGGTGG            684

TTAAGAGCAC CTGCTGCTCT TCCAGAGGAC CTGGGTTCAA TTCCACTTA GATGGCAGCT             744

CAAACTATCT ATAATTCCAA TTCCAAGAA AACTGATGCC CTATTTTGCC CCTTTAGTTA             804

GTAGTATTTA CAGTATTCTT TATAAATTCA CCTTGACATG ACCATCTTGA GCTACAGCCA            864
```

```
TCCTAACTGC  CTCAGAATCA  CTCAAGTTCT  TCCACTCGGT  TTCCCAGCGG  ATTTTAAGTG      924

GATAAACTGT  GAGAGTGGTC  TGTGGGACTT  TGGAATGTGT  CTGGTTCTGA  TAGTCACTTA      984

TGGCAACCCA  GGTACATTCA  ACTAGGATGA  AATAAATTCT  GCCTTAGCCC  AGTAGTATGT     1044

CTGTGTTTGT  AAGGACCCAG  CTGATTTTCC  CACCACCCCT  CCATCAGTCC  GCCACTAATA     1104

AAGTGCATCT  ATGC                                                          1118
```

( 2 ) INFORMATION FOR SEQ ID NO:2:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Pro  Phe  His  Thr  Ala  Leu  Ser  Phe  Leu  Ile  Leu  Thr  Thr  Ala
  1              5                        10                       15

Leu  Gly  Ile  Trp  Ala  Gln  Ile  Thr  His  Ala  Thr  Glu  Thr  Lys  Glu  Val
              20                       25                       30

Gln  Ser  Ser  Leu  Lys  Ala  Gln  Gln  Gly  Leu  Glu  Ile  Glu  Met  Phe  His
            35                       40                       45

Met  Gly  Phe  Gln  Asp  Ser  Ser  Asp  Cys  Cys  Leu  Ser  Tyr  Asn  Ser  Arg
       50                       55                       60

Ile  Gln  Cys  Ser  Arg  Phe  Ile  Gly  Tyr  Phe  Pro  Thr  Ser  Gly  Gly  Cys
 65                       70                       75                       80

Thr  Arg  Pro  Gly  Ile  Ile  Phe  Ile  Ser  Lys  Arg  Gly  Phe  Gln  Val  Cys
                      85                       90                       95

Ala  Asn  Pro  Ser  Asp  Arg  Arg  Val  Gln  Arg  Cys  Ile  Glu  Arg  Leu  Glu
                100                      105                      110

Lys  Asn  Ser  Gln  Pro  Arg  Thr  Tyr  Lys  Gln
                115                      120
```

( 2 ) INFORMATION FOR SEQ ID NO:3:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:3:

```
TTATTTAT                                                                     8
```

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:4:

```
ATAAGAATGC  GGCCGCTGTT  GACAAAGCCA  GATATG                                  36
```

( 2 ) INFORMATION FOR SEQ ID NO:5:

( i ) SEQUENCE CHARACTERISTICS:
   ( A ) LENGTH: 16 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:5:

AACAGCTATG ACCATG 16

( 2 ) INFORMATION FOR SEQ ID NO:6:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:6:

ACAGCTATGA CCATG 15

( 2 ) INFORMATION FOR SEQ ID NO:7:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:7:

GGCCGGGCAT CATCTTTA 18

( 2 ) INFORMATION FOR SEQ ID NO:8:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:8:

ATGGCTTGGT GGTTAAGA 18

( 2 ) INFORMATION FOR SEQ ID NO:9:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:9:

GTAAAACGAC GGCCAGT 17

( 2 ) INFORMATION FOR SEQ ID NO:10:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "DNA"

( x i ) SEQUENCE DESCRIPTION: SEQ ID NO:10:

TTGAACTCAC TAAGACTCC                  19

( 2 ) INFORMATION FOR SEQ ID NO:11:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:11:

GTTTCGGTCT ATCAG                  15

( 2 ) INFORMATION FOR SEQ ID NO:12:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:12:

GGGAATTCCA TATGATCACA CATGCAACAG AGACA                  35

( 2 ) INFORMATION FOR SEQ ID NO:13:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:13:

CGCGGATCCT ATCACACCCT TCTCTAAAGC AAATG                  35

( 2 ) INFORMATION FOR SEQ ID NO:14:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:14:

GTTTCGGTCT ATAC                  14